(12) United States Patent
Takai et al.

(10) Patent No.: US 7,241,857 B2
(45) Date of Patent: Jul. 10, 2007

(54) METHOD FOR PRODUCING ALLYL COMPOUND, AND ETHER OR ESTER COMPOUND PRODUCED THEREBY

(75) Inventors: Masaki Takai, Kanagawa (JP); Yoshiyuki Tanaka, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/300,290

(22) Filed: Dec. 15, 2005

(65) Prior Publication Data

US 2006/0106181 A1  May 18, 2006

Related U.S. Application Data

(62) Division of application No. 10/648,210, filed on Aug. 27, 2003, now Pat. No. 7,119,222.

(30) Foreign Application Priority Data

Aug. 30, 2002 (JP) ............................. 2002-252900
Sep. 5, 2002 (JP) ............................. 2002-260452
Sep. 6, 2002 (JP) ............................. 2002-261870

(51) Int. Cl.
*C08G 65/34* (2006.01)
*C08F 20/10* (2006.01)

(52) U.S. Cl. ...................... 528/425; 525/298; 525/300; 526/318; 560/265

(58) Field of Classification Search ............... 528/425; 525/298, 300; 526/318; 560/265; 425/298, 425/300

See application file for complete search history.

(56) References Cited

U.S. PATENT DOCUMENTS 5,578,740 A  11/1996 Au et al.
6,525,228 B2  2/2003 Chauvin et al.
2005/0075518 A1  4/2005 Takal et al.

FOREIGN PATENT DOCUMENTS

JP  2-172924  7/1990

OTHER PUBLICATIONS

C. Goux, et al., Organometallics, vol. 14, No. 10, pp. 4585-4593, "Stereo- and Regioselectivity in Palladium-Catalyzed Allylic Etherification", 1995.
T. Ikariya, et al., Japan Society for the Promotion of Science, the 116th Committee Meeting, Joint Subcommittee Meeting Reports, pp. 46-49, "Direct Transformation of Allylic Alcohols Catalyzed by Palladium-Phosphite Complexes", 2002 (with English translation).
T. Koda, et al., Graduate School of Science and Engineering, Tokyo Institute of Technology, CREST, vol. 79, No. 2, p. 1194, "Dehydrative Etherification of Allyl Alcohols Catalized by Palladium-Phosphite Complex", 2001 (with English translation).
C. Thorey, et al., Tetrahedron Letters, vol. 36, No. 31, pp. 5527-5530, "Diastereoselective Synthesis of Vinylmorpholines by Palladium-Catalyzed Tandem Allylic Substitutions Using Enantiopure Aminoalcohols as Bifunctional Nucleophiles", 1995.
B. M. Trost, et al., J. Am. Chem. Soc., vol. 120, No. 8, pp. 1732-1740, "Total Synthesis of (±)-and (+)-Valienamine Via a Strategy Derived From New Palladium-Catalyzed Reactions", 1998.
K. Pachamuthu, et al., Tetrahedron Letters, vol. 39, pp. 5439-5442, "Palladium Catalysed Regio and Stereoselective Reduction of Baylis-Hillman Coupling Products Derived Allylic Acetates", 1998.
J. Tsuji, et al., Bulletin of the Chemical Society of Japan, vol. 49, No. 6, pp. 1701-1702, "Preparation of Matsutake Alcohol (1-OCTEN-3-OL) From a Butadiene Telomer", Jun. 1976.
J. Ross, et al., Organometallics, vol. 20, No. 1, pp. 138-142, "Ligand Effects in Palladium-Catalyzed Allylic Alkylation in Ionic Liquids", 2001.
N. Yoshimura, et al., The Chemical Society of Japan, No. 2, pp. 119-127, "New Processes for 1-Octanol and Various Diols by Noble Metal Complex Catalysts", 1993.

*Primary Examiner*—Duc Truong
(74) *Attorney, Agent, or Firm*—Oblon, Spivak, McClelland, Maier & Neustadt, P.C.

(57) ABSTRACT

A method for producing an allyl compound having a compositional formula different from that of an allyl starting material compound, which comprises reacting the allyl starting material compound with an oxygen nucleophilic agent in the presence of a catalyst containing at least one transition metal compound containing a transition metal selected from the group consisting of transition metals belonging to Group 8 to Group 10 of the Periodic Table and a multidentate phosphite compound.

24 Claims, No Drawings

METHOD FOR PRODUCING ALLYL COMPOUND, AND ETHER OR ESTER COMPOUND PRODUCED THEREBY

This application is a DIV of Ser. No. 10/648,210 filed Aug. 27, 2003 now U.S. Pat. No. 7,119,222.

BACKGROUND OF THE INVENTION

1. Field of the Invention

The present invention relates to a method for producing a new allyl compound different from an allyl starting material compound by reacting the allyl starting material compound with an oxygen nucleophilic agent in the presence of a catalyst, and an ether or ester compound produced thereby.

2. Prior Arts

Various kinds of new allyl compounds can be synthesized by carrying out a catalytic reaction using a transition metal compound and using an allyl compound as a starting material. This reaction proceeds as illustrated in the following reaction formula, wherein an allyl starting material compound having an eliminating group X is n-coordinated and oxidatively added to a transition metal compound to form a n-allyl complex having three carbons of the allyl part bonded to a metal and the terminal allyl carbon of the n-allyl complex is attacked by a nucleophilic agent expressed by Nu-H or Nu⁻.

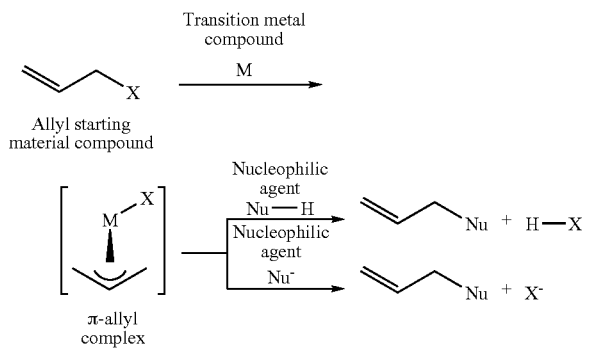

The synthesizing reaction of an allyl compound is generally fully described in "Palladium Reagents and Catalysts-Innovations in Organic Synthesis-" published by John Wiley & Sons Company, and various products in a form of allylated nucleophilic agent can be obtained by electing a kind of a nucleophilic agent in the reaction. Among them, when the nucleophilic agent is an oxygen nucleophilic agent such as alcohols, phenols, or carboxylic acids, respective allyl alkyl ether, allyl phenyl ether or allyl carboxylate esters are synthesized, and they are considered to be one of basic reactions useful in synthetic chemistry.

However, as a reaction example of an allyl starting material compound and an oxygen nucleophilic agent, the case in which the oxygen nucleophilic agent is carboxylic acid anion, is generally well known, but there are not so many reaction examples with other oxygen nucleophilic agents due to their low reactivity.

For example, as described in "Organometallics, 1995, 14, p. 4585" illustrating a reaction example with phenols, a synthesis example of allyl phenyl ethers by a palladium catalyst system having a triaryl type monodentate phosphite ligand such as triphenyl phosphite is well known, but its activity is not sufficient.

Also, reaction examples with alcohols are very limited due to low nucleophilic attacking property of alcohol oxygen. As a reaction example between molecules of alcohol oxygen and an allyl starting material compound, dehydration condensation reaction of an allyl alcohol by a catalyst system using a monodentate phosphite ligand of triphenyl phosphite or triethyl phosphite was reported in "Nihon Kagakukai Kouen Yokoushuu, 2001, Vol. 79th, No. 2, p. 1194" and "Nihon Gakujutsu Shinkoukai Souzou Kinou Kagaku Dai 116 Iinkai 2002, 6, Godou Bunkakai Shiryou p. 46". Also, a reaction of alcohols with an allyl alcohol by a catalyst system comprising triphenylphosphite considered to have a highest activity was also reported. However, its catalyst activity is still not high.

As an example of attacking a n-allyl complex by other alcohol oxygen, there are known some cyclizing reactions wherein the cyclization is carried out intramolecularly by attacking n-allyl terminal carbon with alcohol oxygen present at such a position as to form a 5-membered ring or a 6-membered ring in the reaction process. For example, as described in "Tetrahedron Lett., 1995, 36, p. 5527", there is known a synthesis example of a morpholine derivative by a palladium catalyst system having triisopropyl phosphite as a monodentate phosphite ligand. Also, a synthesis example of a 5-membered cyclic product by a palladium catalyst system having a bidentate phosphite ligand having cyclic both terminals composed of a pentan-2,5-diyl group was reported in "J. Am. Chem. Soc., 1998, 120, p. 1732". However, it is necessary for these reactions that an oxygen nucleophilic agent is present at such a position as to easily form a ring, and they are allylation reaction which can proceed only intramolecularly and which is a special system.

When carrying out allylation reaction using the above-mentioned catalyst on an industrial scale, it is strongly demanded to improve a reactivity in order to reduce an amount of expensive palladium used, which is a noble metal, or to make a reactor size smaller, thereby reducing a manufacturing cost. As a method for improving the reactivity, there is a method for having a counter cation of a nucleophilic agent present in the reaction system. As its effect, a nucleophilic agent forming a pair or a coexistent state with such a counter cation increases its nucleophilic attacking force, thereby improving the reactivity.

As some examples, a reaction of cyclopentadiene monoxide and an acetic acid anion is reported in "Organic Syntheses, 1998, 67, p 114", and in order to improve the reactivity, a sodium ion is used as a counter cation for acetic anion in this reaction. However, when such an alkali metal is a counter cation, +1 valent charge is concentrated on one small metal ion, and accordingly there is a tendency of forming a strong ion pair with a nucleophilic agent of a counter anion. Consequently, the attacking force of such a nucleophilic agent is not sufficiently high.

For example, it is reported in "Tetrahedron Lett., 1998, 39, p 5439" that an allyl starting material compound and a formic acid anion are reacted by using a palladium catalyst comprising a triisopropyl phosphite ligand of trialkyl type monodentate phosphite in the presence of ammonium comprising triethylamine having a proton coordinate-bonded, but this reaction is a reaction different from a reaction of an ordinary allyl starting material compound and a nucleophilic agent. That is, the formic acid anion does not form allyl formate by attacking a n-allyl complex as an intermediate but is coordinated to palladium, and carbon dioxide is eliminated and a hydride formed as this result reacts with the n-allyl complex to provide a product of a structure having the allyl starting material reduced.

As mentioned above, although it is possible to produce ether compounds or ester compounds important in organic synthesis by their reaction of an allyl starting material compound and its different oxygen nucleophilic agent, a highly active catalyst system which can sufficiently react an oxygen nucleophilic agent having a low reactivity has not been developed, and therefore practical reaction examples are actually limited. Particularly, in the reaction with alcohols, it is impossible to sufficiently proceed the reaction unless a special environment such as the above-mentioned intramolecular cyclization reaction is provided. Therefore, it has been demanded to develop a new catalyst system which achieves a sufficiently high catalyst activity even in the reaction with such an oxygen nucleophilic agent as having a low reactivity.

The present invention has been made for solving the above-mentioned problems. Thus, an object of the present invention is to provide a method for producing an allyl compound, which can efficiently produce various allyl compounds by using a new catalyst system achieving an especially high activity to such an oxygen nucleophilic agent as having a low reactivity in the reaction of an allyl starting material compound and an oxygen nucleophilic agent, and to provide an ether compound and an ester compound.

The present inventors have intensively studied to develop a catalyst system capable of efficiently proceeding a reaction among molecules of various allyl starting material compounds and their different oxygen nucleophilic agents, and have discovered that a catalyst system comprising a multidentate phosphite compound and a transition metal compound of Group 8 to Group 10 of the Periodic Table achieves an unexpectedly very high activity as compared with a conventional catalyst system of monodentate phosphine or bidentate phosphine and a catalyst system of triphenyl phosphite known as a prior art. The present invention has been accomplished on the basis of this discovery.

SUMMARY OF THE INVENTION

That is, the essential feature of the present invention resides in a method for producing a new allyl compound having a compositional formula different from that of an allyl starting material compound, which comprises reacting the allyl starting material compound with an oxygen nucleophilic agent in the presence of a catalyst containing at least one transition metal compound containing a transition metal selected from the group consisting of transition metals belonging to Group 8 to Group 10 of the Periodic Table and a multidentate phosphite compound.

DETAILED DESCRIPTION OF THE PREFERRED EMBODIMENTS

Hereinafter, the present invention is described in more details.

A method for producing an allyl compound in accordance with the present invention (hereinafter referred to as "production method of the present invention") produces a new allyl compound having a compositional formula different from an allyl starting material compound by reacting the allyl starting material compound with an oxygen nucleophilic agent in the presence of a catalyst containing the following specific transition metal compound and the following multidentate coordinated phosphite compound.

First, the allyl starting material compound used in the production method of the present invention is explained hereinafter. The allyl starting material compound is not specially limited so long as it has an allyl group and an eliminating group in a molecule, but has a total molecular weight of at most 1,500 (about at most 100 carbon atoms), and it is preferable that under reaction conditions, a part or all of the allyl starting material compound is soluble in a solvent, compatible with an oxygen nucleophilic agent, or meltable by melting with heat. Among them, a preferable example is a compound having such a structure as expressed by the following formula (a) wherein an eliminating group expressed by X is bonded to an allyl-group having a group expressed by $R^a$ to $R^e$. The eliminating group means an atom or an atom group which is bonded to carbon of a substrate structure (allyl structure in the present invention) as a matrix and is generally an electron withdrawing group and is eliminated from the substrate molecule having an electron pair.

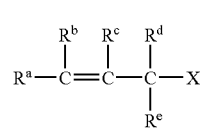

(a)

In the above formula (a), $R^a$ to $R^e$ are respectively independently a hydrogen atom, a halogen atom, a hydroxy group, an amino group, a formyl group, a chain-like or cyclic alkyl group, an aryl group, an alkoxy group, an aryloxy group, an alkylthio group, an arylthio group, an amide group, an acyl group or an acyloxy group (in the present specification, the aryl group includes a heterocyclic compound forming an aromatic 6π electron cloud on the upper and lower parts of the ring). The above illustrated groups may further have a substituent. Examples of the substituent are not specially limited so long as they do not affect adversely the reaction system, but preferable examples include a halogen atom, a hydroxy group, an amino group, a formyl group, an alkyl group, an aryl group, an alkoxy group, an aryloxy group, an alkylthio group, an arylthio group, an amide group, an acyl group or an acyloxy group.

Preferable examples of the above $R^a$ to $R^e$ include a hydrogen atom, a halogen atom, a hydroxy group, an amino group, a chain-like or cyclic alkyl group which may be substituted with the above substituents, an aryl group which may be substituted with the above substituents, an alkoxy group which may be substituted with the above substituents, an aryloxy group which may be substituted with the above substituents, an alkylthio group, an arylthio group, an acyl group or an acyloxy group, and more preferable examples include a hydrogen atom, a halogen atom, a hydroxy group, an amino group, a chain-like or cyclic alkyl group which may be substituted with the above substituents, an aryl group which may be substituted with the above substituents, an alkoxy group, an arylalkoxy group, an aryloxy group, an alkylaryloxy group, an alkylthio group, an arylthio group, an acyl group or an acyloxy group.

The carbon number of $R^a$ to $R^e$ is generally at most 40, preferably at most 30, more preferably at most 20. When $R^a$ to $R^e$ is a group containing a carbon chain, the group may have at least one carbon-carbon double bond or triple bond in the carbon chain.

Among the above illustrated groups, particularly preferable $R^a$ to $R^e$ are respectively independently a hydrogen atom, a substituted or unsubstituted alkyl group or a substituted or unsubstituted aryl group.

Also, a group adversely affecting the reaction system is a material poisoning a catalyst such as a group containing conjugated diene, a material oxidizing and decomposing a phosphite compound such as a group containing peroxide or the like. Accordingly, in the present specification, a group "having no adverse affection on the reaction system" means to exclude these groups adversely affecting the reaction system.

On the other hand, examples of the eliminating group X include a halogen atom, a hydroxy group, a nitro group, an amino group expressed by $R'_2N-$, a sulfonyl group expressed by $RSO_2-$, a sulfonate group expressed by $RSO_2O-$, an acyloxy group expressed by $RC(=O)O-$, a carbonate group expressed by $R'OC(=O)O-$, a carbamate group expressed by $R'NHC(=O)O-$, a phosphate group expressed by $(R'O)_2P(=O)O-$, an alkoxy or aryloxy group expressed by $RO-$. In the above formulae, R is a monovalent organic group and R' is a hydrogen atom or a monovalent organic group. The kind of the organic group is not specially limited so long as it does not adversely affect the reaction system, but preferable examples include an alkyl group or an aryl group. When R is an organic group, its carbon number is generally from 1 to 40, preferably from 1 to 30, more preferably from 1 to 20. When the eliminating group X is a group containing a carbon chain, it may have at least one carbon-carbon double or triple bond in a carbon chain.

Among the above illustrated examples, X is preferably a hydroxyl group, an acyloxy group having a structure expressed by $-C(=O)O-$, a carbonate group, a carbamate group, a phosphate group having a structure expressed by $=P(=O)-$ or a sulfonate group having a structure expressed by $-S(=O)_2O-$, and particularly preferable examples include a hydroxyl group, an acyloxy group and a carbonate group. Examples of the acyloxy group include a $C_1-C_6$ acyloxy group such as an acetoxy group, a propionyloxy group, a butyryloxy group or an isobutyryloxy group. Examples of the carbonate group include a $C_1-C_6$ alkylcarbonate group such as a methylcarbonate group, an ethylcarbonate group or a $C_6-C_{12}$ arylcarbonate group such as a phenylcarbonate group. A particularly preferable example of X is a hydroxyl group and an acyloxy group, and most preferable example of X is an acetoxy group.

Among the above $R^a$ to $R^e$ and X, at least two optional groups may be bonded to each other to form at least one cyclic structure. However, when X is contained in a stable cyclic structure, it is not preferable since X is hardly eliminated. The number of cyclic structures is not specially limited, but is generally from 0 to 3, preferably from 0 to 2, particularly preferably from 0 or 1. Also, the number of atoms forming each ring is not specially limited, but is usually 3 to 10-membered ring, preferably 4 to 9-membered ring, particularly preferably 5 to 7-membered ring. When a plurality of rings are present, these rings may be partly commonly owned to form a condensed ring structure.

When at least two groups of $R^a$ to $R^e$ and X are bonded to form a cyclic structure, its carbon number is usually 0 to 40×p, preferably 0 to 30×p, more preferably 0 to 20×p, wherein p is a number of groups participating in the formation of the ring structure.

Examples of the allyl starting material compound expressed by the above formula (a) include preferably halogenated allyls, allyl alcohols, allylamines, allyl sulfones, allyl sulfonates, allyl esters of carboxylic acids, allyl carbonates, allyl carbamates, allyl esters of phosphoric acid, allyl ethers, vinyl ethylene oxides, and the like.

Examples of the halogenated allyls include allyl chloride, 2-butenyl bromide, 1-chloro-2-phenyl-2-pentene and the like.

Examples of the allyl alcohols include 2-butenyl alcohol, 2,3-dimethyl-2-butenyl alcohol, 3-bromoallyl alcohol, cinnamyl alcohol, crotyl alcohol, 3-methyl-2-cyclohexene-1-ol, 3-methyl-2-butene-1-ol, geraniol, 2-pentene-1-ol, 3-butene-2-ol, 1-hexene-3-ol, 2-methyl-3-phenyl-2-propene-1-ol, 1-acetoxy-4-hydroxycyclopentene-2,1,2-dihydrocatechol, 3-hexene-2,5-diol, and the like.

Examples of the allylamines include allyldiethylamine, 3-methoxyallyldiphenylamine, triallylamine, 2-butenyldibenzylamine, and the like.

Examples of the allyl sulfones include allylphenyl sulfone, methylyl-p-tolylsulfone, 2-methyl-3-sulfolene, 1,3-diphenylallylmethylsulfone, and the like.

Example of the allyl sulfonates include allyl toluene-4-sulfonate, 3-thiophenmethanesulfonate, 4-chloro-2-butenylmethanesulfonate, and the like.

Example of the allyl esters of carboxylic acid include allyl acetate, 2-hexenyl acetate, 2,4-hexadienyl acetate, prenyl acetate, geranyl acetate, farnesyl acetate, cinnamyl acetate, rinaryl acetate, 3-butene-2-yl acetate, 2-cyclopentenyl acetate, 2-trimethylsilylmethyl-2-propenyl acetate, 2-methyl-2-cyclohexenyl acetate, 1-phenyl-1-butene-3-yl propionate, 1-cyclohexyl-2-butene butyrate, 4-cyclopenten-1,3-diol-1-acetate, 1,4-diacetoxy-2-butene, 3-acetoxy-4-hydroxy-1-butene, and the like.

Example of the allyl carbonates include allylmethyl carbonate, 4-acetoxy-2-butenylethyl carbonate, nerylmethyl carbonate and the like.

Examples of the allyl carbamates include allyl-N-(4-fluorophenyl)carbamate, 2-butenyl-N-methyl carbamate, furfuryl-N-(2-methoxydiphenyl)carbamate and the like.

Examples of the allylesters of phosphoric acid include allyldimethyl phosphate, 3-methyl-2-butenyldiphenyl phosphate, methylethylfurfuryl phosphate and the like.

Examples of the allyl ethers include allyl ethyl ether, allyl phenyl ether, 2,3-diphenylallylyisopropyl ether, 2-butenyl-4-fluorophenyl ether and the like.

Examples of the phenylethylene oxides include butadiene monoxide, cyclopentadiene monoxide, 1,3-cyclohexadiene monoxide and the like.

Particularly preferable examples of the allyl starting material compound include a mixture of at least two compounds selected from the group consisting of 3,4-disubstituted 1-butene expressed by the following formula (b), 1,4-disubstituted 2-butene expressed by the following formula (c) and their compounds.

$$CH_2=CH-CHR^1-CH_2R^2 \qquad (b)$$

In the above formula (b), $R^1$ and $R^2$ are respectively independently an acetoxy group or a hydroxyl group. Examples of the 3,4-disubstituted 1-butene expressed by the above formula (b) include 3,4-diacetoxy-1-butene, 3-acetoxy-4-hydroxy-1-butene, 4-acetoxy-3-hydroxy-1-butene, 3,4-dihydroxy-1-butene, and the like.

$$R^3CH_2-CH=CH-CH_2R^4 \qquad (c)$$

In the formula (c), $R^3$ and $R^4$ are respectively independently an acetoxy group or a hydroxyl group. Examples of the 1,4-disubstituted 2-butene expressed by the above formula (c) include 1,4-diacetoxy-2-butene, 1-acetoxy-4-hydroxy-2-butene, 1,4-dihydroxy-2-butene, and the like.

Next, the oxygen nucleophilic agent used in the production method of the present invention is explained hereinafter. Generally, a nucleophilic agent is a reactive material having a non-covalent electron pair, which is basic and has a tendency of attacking a carbon nucleus, but in the present invention, every reactive material having a non-covalent electron pair on an oxygen atom and having a tendency of attacking an allyl-terminated carbon nucleus of n-allyl complex with the electron pair is used as the oxygen nucleophilic agent.

Examples of the oxygen nucleophilic agent usable in the present invention include a proton adduct compound expressed by AO—H containing a nucleophilic oxygen atom, an anion expressed by AO$^-$ which is a deprotonated material, or a compound which can be an anion in the reaction system. In the above formula, A is a hydrogen atom or an organic group. The organic group is a material having a carbon atom, a nitrogen atom, a phosphorus atom or a sulfur atom bonded to the nucleophilic oxygen atom, which becomes a liquid in the reaction system and does not adversely affect the reaction system. The carbon number of the organic group is generally in a range of from 1 to 40 so that it can be easily soluble in the reaction system, and the carbon number is preferably from 1 to 30, more preferably from 1 to 20.

Examples of the organic group bonded to the nucleophilic oxygen atom by way of a carbon atom include an unsubstituted or substituted chain-like or cyclic alkyl group, an unsubstituted or substituted aryl group or an acyl group.

Examples of the organic group bonded to the nucleophilic oxygen atom by way of a nitrogen atom include an unsubstituted or substituted amino group or a group having a C=N bond.

Examples of the organic group bonded to the nucleophilic oxygen atom by way of a phosphorus atom include an unsubstituted or substituted phosphonate group, an unsubstituted or substituted phosphinate group or an unsubstituted or substituted phosphinoyl group.

Examples of the organic group bonded to the nucleophilic oxygen atom by way of a sulfur atom include an unsubstituted or substituted sulfonyl group.

Substituents of the above illustrated groups are not specially limited so long as they are an organic group and do not adversely affect the reaction system, and preferable examples include a chain-like or cyclic alkyl group, an aryl group, an alkoxy group, an arylalkoxy group, an aryloxy group, an alkylaryloxy group, an alkylthio group, an arylthio group, an acyl group or an acyloxy group. When the above illustrated groups have these substituents, the total carbon number including substituents should be within the above-mentioned range.

However, even when an oxygen nucleophilic agent is within the above-mentioned definition, it is necessary to exclude such an oxygen nucleophilic agent as to be the same as substituent (X or its anion X$^-$ in the above formula (a)) or its proton adduct (X—H), which is eliminated from an allyl starting material compound depending on the reaction, since it provides such a state as not proceeding the reaction apparently or such a state as producing an isomerized material only of the allyl starting material compound as a product. Also, it is necessary to exclude such an oxygen nucleophilic agent as to be completely the same as the allyl starting material compound, and for example, when the oxygen nucleophilic agent and the allyl starting material compound are both allyl alcohols, its product is limited to a diallyl ether having a structure obtained by simple dehydration condensation of the starting material, as previously described with regard to the prior art. Such an oxygen nucleophilic agent should be excluded since it is less important in respect of carrying out a wide variety of synthesis.

Among the above explained oxygen nucleophilic agents, a preferable oxygen nucleophilic agent is a material having a total molecular weight of at most 400 (about at most 30 carbon atoms), a part or all of which is soluble in a solvent, compatible with an allyl starting material compound, or meltable by melting with heat.

Examples of an oxygen nucleophilic agent in a proton adduct form (AO—H) are illustrated below. When A is a hydrogen atom, it is water.

When A is an organic group having a nucleophilic oxygen bonded a carbon atom, their examples include hydroxy compounds, carboxylic acids, thiocarboxylic acids or selenocarboxylic acids.

Examples of the hydroxy compounds include alcohols such as methanol, ethanol, n-propanol, n-butanol, sec-butanol, t-butanol, allyl alcohol, 2-ethylhexyl alcohol, 4-chloro-1-butanol, benzyl alcohol, cyclohexanol, ethylene glycol, 1,3-propanediol and 1,4-butanediol; and phenols such as phenol, p-methoxyphenol, 2,4-dimethylphenol, 1-naphthol, 2-naphthol, 3,6-di-t-butyl-2-naphthol, 2-pyridinol or 2-bromo-4-pyridinol.

Examples of the carboxylic acids include aliphatic carboxylic acids such as acetic acid, propionic acid, butyric acid, chloroacetic acid, oxalic acid or adipic acid; and aromatic carboxylic acids such as benzoic acid, naphthalene-2-carboxylic acid, m-cyanobenzoic acid or o-toluic acid.

Examples of the thiocarboxylic acids include a compound expressed by $CH_3C(=S)$—OH or a compound expressed by PhC(=S)—OH.

Examples of the selenocarboxylic acids include a compound expressed by $CH_3C(=Se)$—OH or a compound expressed by PhC(=Se)—OH. In the present specification, Ph means a phenyl group.

When A is an organic group wherein a nucleophilic oxygen and a nitrogen atom are bonded to each other, its examples include hydroxyamines such as N,N-diethylhydroxyamine, N,N-dibenzylhydroxyamine or the like; oximes such as acetone oxime, benzophenone oxime, cyclopentanone oxime or the like; carbamates such as t-butyl-N-hydroxy carbamate or the like; hydroxyimides such as N-hydroxymaleimide, N-hydroxy succinimide or the like; 1-hydroxybenzotriazole, and the like.

When A is an organic group wherein a nucleophilic oxygen and a phosphorus atom are bonded to each other, its examples include phosphinic acids, phosphonic acid esters, phosphoric acid esters, and the like.

Examples of the phosphinic acids include dimethylphosphinic acid, diphenylphosphinic acid or the like; examples of the phosphonic acid esters include ethyl phosphonic acid, propyl phosphonic acid monophenyl ester or the like; and examples of the phosphoric acid esters include diphenyl phosphate, dimethyl phosphate or the like.

When A is an organic group wherein a nucleophilic oxygen and a sulfur atom are bonded to each other, its examples include sulfonic acids such as p-toluenesulfonic acid, methanesulfonic acid, ethanesulfonic acid or the like; and sulfuric acid monoesters such as sulfuric acid monophenylester, sulfuric acid monooctylester or the like.

All of the above illustrated examples are shown in a proton adduct form, but each of the above illustrated compounds includes a deprotonated product or a compound convertible to its deprotonated product in the reaction system. Examples of the compound convertible to its deprotonated product in the reaction system include a compound in which the deprotonated product is bonded to other atom or atom group. Examples of the other atom or atom group bonded to the deprotonated product include various kinds of monovalent cations (such as Na+, K+ or the like).

Among the above illustrated examples, the compound wherein A is an organic group having a nucleophilic oxygen and a carbon atom bonded to each other is particularly preferable, and the following types (i) to (iv) oxygen nucleophilic agents are particularly preferable.

(i) Alcohols expressed by RO—H or RO− (wherein R is an alkyl group which may have a substituent and may have a double bond or a triple bond in a carbon chain) or their deprotonated products.

(ii) Hydroxy aryls expressed by ArO—H or ArO− (wherein Ar is an aryl group which may have a substituent and may contain a hetero atom such as nitrogen, oxygen, phosphorus or sulfur) or their deprotonated products.

(iii) Aliphatic carboxylic acids expressed by R'COO—H or R'COO− (wherein R' is a hydrogen atom or an alkyl group which may have a substituent and may have a double bond or a triple bond in a carbon chain).

(iv) Aromatic carboxylic acids expressed by Ar'COO—H or Ar'COO− (wherein Ar' is an aryl group which may have a substituent and may have a hetero atom such as nitrogen, oxygen, phosphorus or sulfur) or their deprotonated products.

Examples of the type (i) oxygen nucleophilic agent include a saturated or unsaturated alcohol and their substituent-containing products, and a saturated or unsaturated diol, a multi-substituted alcohol or their substituent-containing products.

Examples of the saturated or unsaturated alcohol and their substituent-containing products include methyl alcohol, ethyl alcohol, n-propyl alcohol, i-propyl alcohol, n-butyl alcohol, 2-ethylhexanol, n-octanol, allyl alcohol, crotyl alcohol, benzyl alcohol, 1-bromo-2-propanol, 2-methylcyclopentanol, 2-phenylethanol, neopentyl alcohol, 4-cyclohexenol, cholesterol and the like. Examples of the saturated or unsaturated diol, the multi-substituted alcohol or their substituent-containing products include 1,2-ethane diol, 1,3-propane diol, 1,4-buthane diol, 2-butene-1,4-diol, 2-chloro-1,3-propane diol, 1,2-cyclopentane diol, glycerin, pentaerythritol and the like.

Among the type (i) oxygen nucleophilic agents, a saturated alcohol or a saturated diol is preferable, examples of which include methyl alcohol, ethyl alcohol, n-propyl alcohol, i-propyl alcohol, n-butyl alcohol, 2-ethylhexanol, n-octanol and a $C_1$–$C_{10}$ diol such as 1,2-ethanediol, 1,3-propane diol or 1,4-buthane diol.

Examples of the type (ii) oxygen nucleophilic agents include monohydroxy aryl and their substituent-containing products, and di- or polyhydroxy aryl and their substituent-containing products. Examples of the monohydroxy aryl and their substituent-containing products include phenol, cresol, 4-nitrophenol, 2-fluorophenol, 2,4-di-t-butylphenol, 2,4-di-t-butyl-6-methylphenol, 1-naphthol, 2-naphthol, 3-t-butyl-2-naphthol or the like. Examples of the di- or polyhydroxy aryl and their substituent-containing products include catechol, resorcinol, hydroquinone, 2,4-dihydroxyphenyl ethyl ketone, 4-n-hexyl resorcinol, 1,8-dihydroxy naphthalene, 1,2-dihydroxy naphthalene, 1-methyl-2,3-dihydroxy naphthalene, 1,2,4-benzene triol or the like.

Among the type (ii) oxygen nucleophilic agents, monohydroxy aryl or dihydroxy aryl is preferable, examples of which include a $C_1$–$C_{15}$ hydroxyaryl such as phenol, 1-naphthol, 2-naphthol, catechol, resorcinol, hydroquinone or 2,6-dihydroxy naphthalene.

Examples of the type (iii) oxygen nucleophilic agents include a saturated aliphatic carboxylic acid and their substituent-containing products, an unsaturated aliphatic carboxylic acid and their substituent-containing products, and aliphatic dicarboxylic acids and their substituent-containing products, and the like. Examples of the saturated aliphatic carboxylic acid and their substituent-containing products include acetic acid, propionic acid, butyric acid, valeric acid, caproic acid, lauric acid, cyclohexane carboxylic acid, α-methyl butyric acid, γ-chloro-α-methyl valeric acid, α-hydroxy propionic acid, γ-phenyl butyric acid, and the like. Examples of the unsaturated aliphatic carboxylic acid and their substituent-containing products include acrylic acid, oleic acid, linolic acid, linolenic acid, 2-cyclohexene carboxylic acid, 4-methoxy-2-butenoic acid, methacrylic acid, and the like. Examples of the aliphatic dicarboxylic acid and their substituent-containing products include oxalic acid, malonic acid, succinic acid, glutaric acid, adipic acid, maleic acid, fumaric acid, and the like.

Among the type (iii) oxygen nucleophilic agents, a saturated aliphatic carboxylic acid or a saturated aliphatic dicarboxylic acid is preferable, examples of which include a $C_1$–$C_{20}$ aliphatic carboxylic acid such as acetic acid, propionic acid, butyric acid, valeric acid, caproic acid, lauric acid, myristic acid, palmitic acid, stearic acid, oxalic acid, malonic acid, succinic acid, glutaric acid, adipic acid, and the like.

Examples of the type (iv) oxygen nucleophilic agents include an aromatic carboxylic acid and their substituent-containing products, and an aromatic di- or polycarboxylic acid and their substituent-containing products. Examples of the aromatic carboxylic acid and their substituent-containing products include benzoic acid, 3-cyanobenzoic acid, 2-bromobenzoic acid, 2,3-dimethoxybenzoic acid, 4-phenoxybenzoic acid, p-nitrobenzoic acid, m-toluic acid, o-methoxybenzoic acid, phthalic acid monomethyl ester, terephthalic acid monoethyl ester, naphthalene-1-carboxylic acid, 1-methylnaphthalene-2-carboxylic acid, 2-ethoxynaphthalene-1-carboxylic acid, 1-hydroxynaphthalene-2-carboxylic acid, 1-bromonaphthalene-2-carboxylic acid, anthracene-9-carboxylic acid, phenanthrene-4-carboxylic acid, picolinic acid, nicotinic acid, isonicotinic acid, 2-methoxythionicotinic acid, 6-chloronicotinic acid, isoquinoline-1-carboxylic acid, quinoline-3-carboxylic acid, quinoline-4-carboxylic acid, 4-methoxyquinoline-2-carboxylic acid, and the like. Examples of the aromatic di- or polycarboxylic acid and their substituent-containing products include phthalic acid, isophthalic acid, terephthalic acid, benzene-1,2,4-tricarboxylic acid, benzene-1,2,4,5-tetracarboxylic acid, naphthalene-1,4-dicarboxylic acid, naphthalene-1,8-dicarboxylic acid, naphthalene-2,3-dicarboxylic acid, naphthalene-2,6-dicarboxylic acid, naphthalene-1,4,5,8-tetracarboxylic acid, and the like.

Among the type (iv) oxygen nucleophilic agents, an aromatic carboxylic acid or dicarboxylic acid is preferable, examples of which include a $C_6$–$C_{15}$ aromatic carboxylic acid such as benzoic acid, naphthalene-2,6-dicarboxylic acid, phthalic acid, isophthalic acid or terephthalic acid.

Hereinafter, a catalyst used in the production method of the present invention is explained in details. The catalyst used in the present invention contains at least one transition metal compound and a multidentate coordinated phosphite compound.

The transition metal compound used in the present invention is at least one kind of compound containing a transition metal selected from the group consisting of transition metals belonging to Group 8 to Group 10 of the Periodic Table (according to IUPAC Inorganic Chemistry Nomenclature, Revised Edition, 1998). Examples of the transition metal compound include an iron compound, a ruthenium compound, an osmium compound, a cobalt compound, a rhodium compound, an iridium compound, a nickel compound, a palladium compound and a platinum compound, and among them, a ruthenium compound, a rhodium compound, an iridium compound, a nickel compound, a palladium compound and a platinum compound are preferable, and a nickel compound, a palladium compound and a platinum compound are more preferable, and a palladium compound is particularly preferable. Kinds of these compounds are optional, examples of which include compounds of the above-mentioned transition metals such as an acetyl acetonate compound, a halide, a sulfate, a nitrate, an organic salt, an inorganic salt, an alkene-coordinated compound, an amine-coordinated compound, a pyridine-coordinated compound, a carbon monoxide-coordinated compound, a phosphine-coordinated compound, a phosphite-coordinated compound or the like.

Examples of the above transition metal compounds are illustrated below. Examples of the iron compound include $Fe(OAc)_2$, $Fe(acac)_3$, $FeCl_2$, $Fe(NO_3)_3$ or the like. Examples of the ruthenium compound include $RuCl_3$, $Ru(OAc)_3$, $Ru(acac)_3$, $RuCl_2(PPh_3)_3$ or the like. Examples of the osmium compound include $OsCl_3$, $Os(OAc)_3$ or the like. Examples of the cobalt compound include $Co(OAc)_2$, $Co(acac)_2$, $CoBr_2$, $Co(NO_3)_2$ or the like. Examples of the rhodium compound include $RhCl_3$, $Rh(OAc)_3$, $[Rh(OAc)_2]_2$, $Rh(acac)(CO)_2$, $[Rh(OAc)(cod)]_2$, $[RhCl(cod)]_2$ or the like. Examples of the iridium compound include $IrCl_3$, $Ir(OAc)_3$, $[IrCl(cod)]_2$ or the like. Examples of the nickel compound include $NiCl_2$, $NiBr_2$, $Ni(NO_3)_2$, $NiSO_4$, $Ni(cod)_2$, $NiCl_2(PPh_3)_3$ or the like. Examples of the palladium compound include $Pd(0)$, $PdCl_2$, $PdBr_2$, $PdCl_2(cod)$, $PdCl_2(PPh_3)_2$, $Pd(PPh_3)_4$, $Pd_2(dba)_3$, $K_2PdCl_4$, $K_2PdCl_6$, $PdCl_2(PhCN)_2$, $PdCl_2(CH_3CN)_2$, $Pd(dba)_2$, $Pd(NO_3)_2$, $Pd(OAc)_2$, $Pd(CF_3COO)_2$, $PdSO_4$, $Pd(acac)_2$, other carboxylate compounds, an olefin-containing compound, an organic phosphine-containing compound such as $Pd(PPh_3)_4$, allyl palladium chloride dimer, or the like. Examples of the platinum compound include $Pt(acac)_2$, $PtCl_2(cod)$, $PtCl_2(CH_3CN)_2$, $PtCl_2(PhCN)_2$, $Pt(PPh_3)_4$, $K_2PtCl_4$, $Na_2PtCl_6$, $H_2PtCl_6$ or the like. In the above illustrations, "cod" means "1,5-cyclooctadiene", "dba" means "dibenzylideneacetone", "acac" means "acetylacetonate", and "Ac" means "acetyl group".

Kinds of the transition metal compounds are not specially limited, and may be a monomer, a dimer and/or a polymer so long as they are an active metal complex.

An amount of the transition metal compound used in the present invention is not specially limited, but in view of a catalytic activity and economic conditions, it is preferable to use the transition metal compound in an amount of generally at least $1\times10^{-8}$ (0.01 mol ppm) mol equivalent, preferably at least $1\times10^{-7}$ (0.1 mol ppm) mol equivalent, more preferably at least $1\times10^{-6}$ (1 mol ppm) mol equivalent, and generally at most 1 mol equivalent, preferably at most 0.001 mol equivalent, more preferably at most 0.0001 mol equivalent, to the amount of an allyl compound used as a reaction starting material.

On the other hand, kinds of the multidentate phosphite compound used in the present invention are not specially limited so long as it is a phosphite compound which is a chelate ligand to the above-mentioned transition metal compound. The number of coordination dentates is usually from bidentate to tetradentate, preferably bidentate. Also, in order to raise a catalyst activity, it is preferably soluble in the reaction system, and its molecular weight is usually at most 3,000, preferably at most 1,500, and usually at least 250, preferably at least 300, more preferably at least 400.

Among bidentate phosphites, a preferable compound is at least one compound selected from the group consisting of compounds as illustrated by the following formulae (I) to (IV).

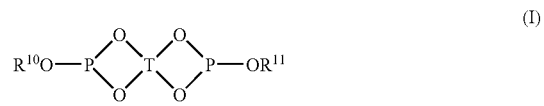

(I)

(II)

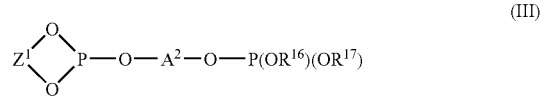

(III)

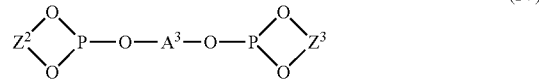

(IV)

In the above formulae (I) to (IV), $R^{10}$ to $R^{17}$ are respectively independently a chain-like or cyclic alkyl group or an aryl group. Examples of the alkyl group include a chain-like alkyl group such as a methyl group, an ethyl group, an n-propyl group, an i-propyl group, an n-butyl group, an i-butyl group, a sec-butyl group, a t-butyl group, a hexyl group, an octyl group and a decyl group; and a cyclic alkyl group such as a cyclopentyl group, a cyclohexyl group and a cycloheptyl group. Examples of the aryl group include a phenyl group, a tolyl group, a xylyl group, a di-t-butylphenyl group, a naphthyl group, a di-t-butylnaphthyl group, a pyridyl group, a pyrrolyl group, a pyrazolyl group, an imidazolyl group, a quinolyl group, an isoquinolyl group, an indolyl group, a furanyl group, a thiophenyl group, an oxazolyl group, and a thiazolyl group.

The above-mentioned alkyl or aryl group may have a substituent. The number of the substituent is not specially limited, but is generally at most 6, preferably at most 4. The substituent is not specially limited so long as it does not adversely affect the reaction system, but its preferable examples include a hydroxyl group, a halogen atom, a cyano group, a nitro group, a formyl group, an alkyl group, an alkoxy group, an aryl group, an aryloxy group, an amino group, an amide group, a perfluoroalkyl group, a trialkylsilyl group, an ester group or the like.

The carbon number of $R^{10}$ to $R^{17}$ is usually from 1 to 40, preferably from 1 to 30, more preferably from 1 to 20. When the above-mentioned alkyl or aryl group has a substituent, the total carbon number of the total group including the substituent should be within the above-mentioned range.

Among the above illustrated groups, in view of stability of the above phosphite, $R^{10}$ to $R^{17}$ are preferably an unsubstituted or substituted aryl group. Examples of the unsubstituted or substituted aryl group include a phenyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 2-ethylphenyl group, a 2-isopropylphenyl group, a 2-t-butylphenyl group, a 2,4-di-t-butylphenyl group, a 2-chlorophenyl group, a 3-chlorophenyl group, a 4-chlorophenyl group, a 2,3-dichlorophenyl group, a 2,4-dichlorophenyl group, a 2,5-dichlorophenyl group, a 3,4-dichlorophenyl group, a 3,5-dichlorophenyl group, a 4-trifluoromethylphenyl group, a 2-methoxyphenyl group, a 3-methoxyphenyl group, a 4-methoxyphenyl group, a 3,5-dimethoxyphenyl group, a 4-cyanophenyl group, a 4-nitrophenyl group, a pentafluorophenyl group, a 1-naphthyl group, a 2-naphthyl group, a 2-methyl-1-naphthyl group, a 3-t-butyl-2-naphthyl group, a 3-methyloxycarbonyl-2-naphthyl group, a 3,6-di-t-butyl-2-naphthyl group, a 5,6,7,8-tetrahydronaphthalene-2-yl group, a 5,6,7,8-tetrahydronaphthalene-1-yl group, and the like.

In the formula (1), T represents a tetravalent organic group. The tetravalent organic group is not specially limited so long as it does not adversely affect the reaction system, but its preferable examples include a carbon atom, an unsubstituted or substituted alkanetetrayl group, an unsubstituted or substituted benzenetetrayl group, or a group having a structure expressed by $T^1$-$(Q^2)_n$-$T^2$. $T^1$ and $T^2$ are respectively independently a trivalent organic group. Preferable examples of the trivalent organic group include an unsubstituted or substituted alkanetriyl group, an unsubstituted or substituted benzenetriyl group or the like. $Q^2$ represents —$CR^{18}R^{19}$— ($R^{18}$ and $R^{19}$ are respectively independently a chain-like or cyclic alkyl group or an aryl group), —O—, —S— or —CO—. n is 0 or 1. The alkyl group or the aryl group of $R^{18}$ and $R^{19}$ are the same as illustrated with regard to the above $R^{10}$ to $R^{17}$.

In the formulae (II) to (IV), $Z^1$ to $Z^3$ and $A^1$ to $A^3$ are respectively independently a bivalent organic group. A kind of the bivalent organic group is not specially limited so long as it does not adversely affect the reaction system, but its preferable examples include an alkylene group, an arylene group, an alkylene-arylene group, or a diarylene group. These organic groups may have a substituent, provided that the substituent does not adversely affect the reaction system. Preferable examples of the substituent include a hydroxyl group, a halogen atom, a cyano group, a nitro group, a formyl group, an alkyl group, an alkoxy group, an aryl group, an aryloxy group, an amino group, an amide group, a perfluoroalkyl group, a trialkylsilyl group and an ester group.

Each carbon number of $Z^1$ to $Z^3$ and $A^1$ to $A^3$ is usually from 1 to 60. Among them, in case of an unsubstituted or substituted alkylene group, an unsubstituted or substituted arylene group or an unsubstituted or substituted alkylene-arylene group, its carbon number is usually at most 40, preferably at most 30, more preferably at most 20. On the other hand, in case of an unsubstituted or substituted diarylene group, its carbon number is usually at most 60, preferably at most 50, more preferably at most 40.

Examples of the unsubstituted or substituted alkylene group include an ethylene group, a tetramethylethylene group, a 1,3-propylene group, a 2,2-dimethyl-1,3-propylene group, a 1,4-butylene group or the like.

Examples of the unsubstituted or substituted arylene group include a 1,2-phenylene group, a 1,3-phenylene group, a 3,5-di-t-butyl-1,2-phenylene group, a 2,3-naphthylene group, a 1,4-di-t-butyl-2,3-naphthylene group, a 1,8-naphthylene group or the like.

Examples of the unsubstituted or substituted alkylene-arylene group include substituents as expressed by the following structural formulae (D-1) to (D-12).

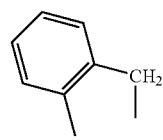

(D-1)

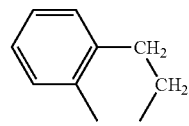

(D-2)

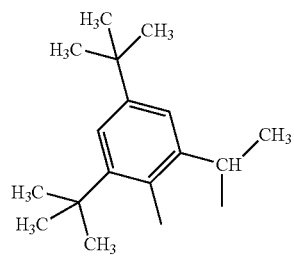

(D-3)

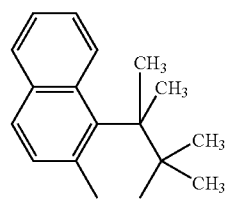

(D-4)

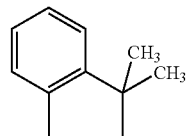

(D-5)

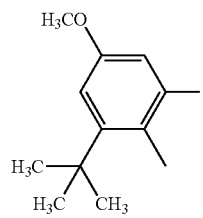

(D-6)

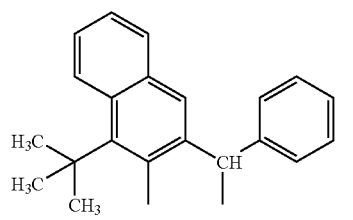

(D-7)

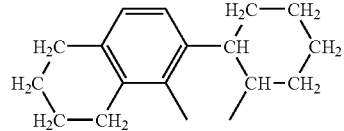

(D-8)

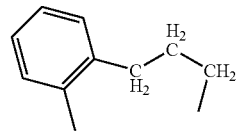

(D-9)

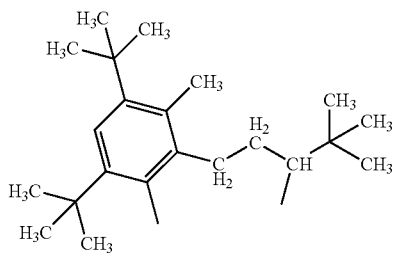
(D-10)

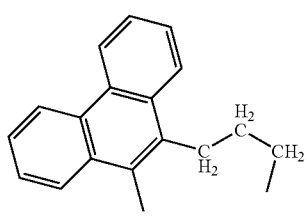
(D-11)

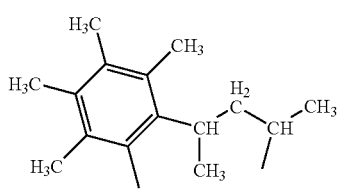
(D-12)

On the other hand, the diarylene group is a group wherein two arylene groups are directly bonded to each other or two arylene groups are bonded to each other by way of a bivalent organic group, and is a group having a structure as expressed by —Ar$^1$-(Q$^1$)$_n$-Ar$^2$—. Ar$^1$ and Ar$^2$ are respectively independently an arylene group which may have a substituent. Q$^1$ is a bivalent organic group, examples of which include —O—, —S—, —CO— or —CR$^{18}$R$^{19}$—. R$^{18}$ and R$^{19}$ are respectively independently a hydrogen atom, a chain-like or cyclic alkyl group which may have a substituent or an aryl group which may have a substituent. n is 0 or 1. The arylene group of Ar$^1$ and Ar$^2$ and the alkyl group and the aryl group of R$^{18}$ and R$^{19}$ may have respectively independently a substituent, preferable examples of which include a hydroxyl group, a halogen atom, a cyano group, a nitro group, formyl group, an alkyl group, an alkoxy group, an aryl group, an aryloxy group, an amino group, an amide group, a perfluoroalkyl group, a trialkylsilyl group, an ester group or the like.

Examples of the arylene group which may have a substituent include groups as illustrated by the following structural formulae (A-1) to (A-48).

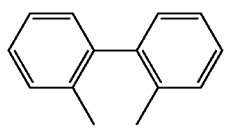
(A-1)

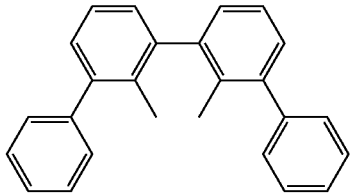
(A-2)

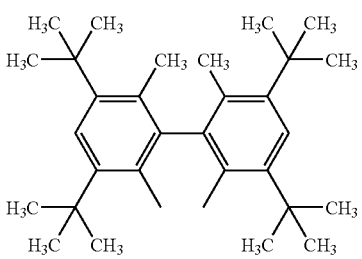
(A-3)

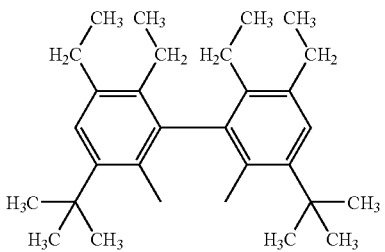
(A-4)

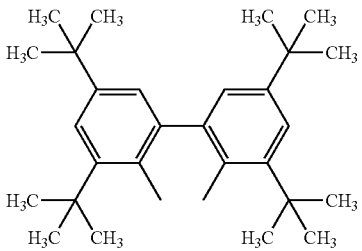
(A-5)

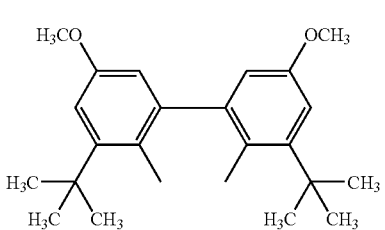
(A-6)

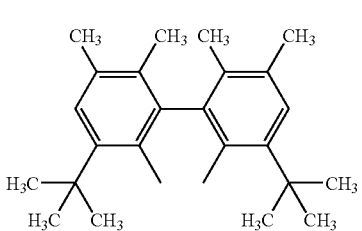
(A-7)

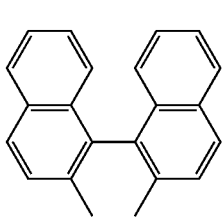
(A-8)

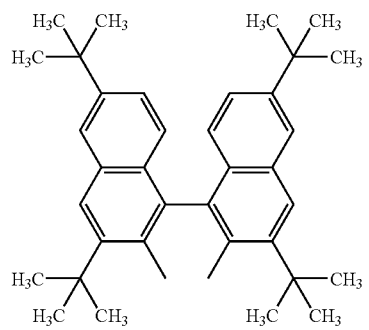
(A-9)
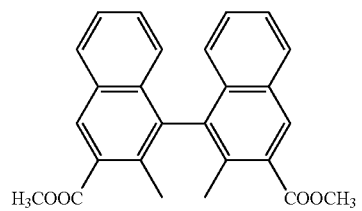
(A-10)
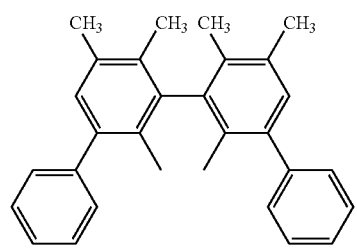
(A-11)
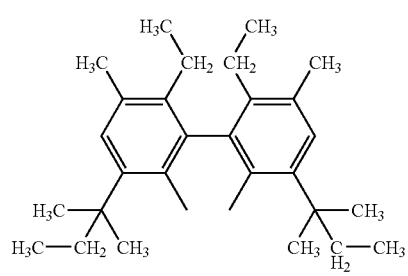
(A-12)
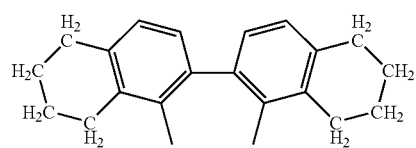
(A-13)
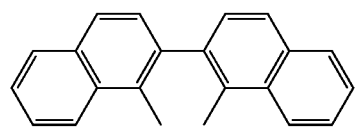
(A-14)
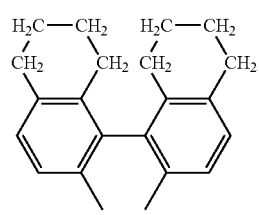
(A-15)
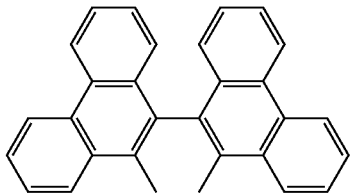
(A-16)
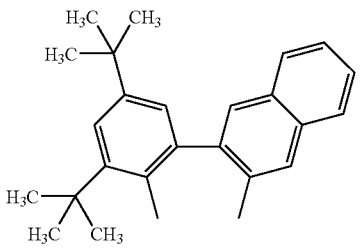
(A-17)
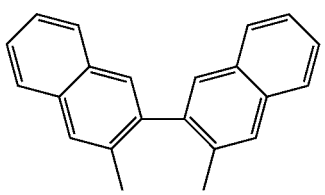
(A-18)
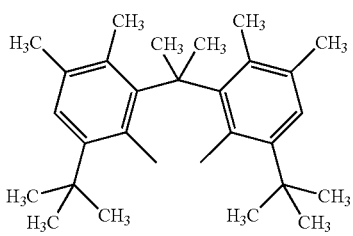
(A-19)
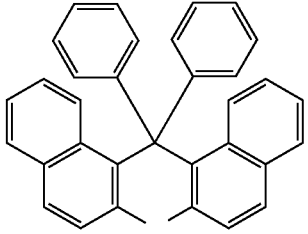
(A-20)
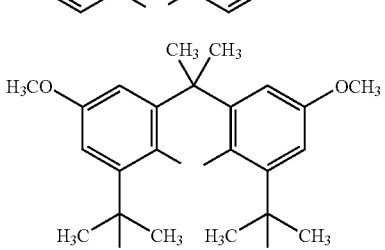
(A-21)
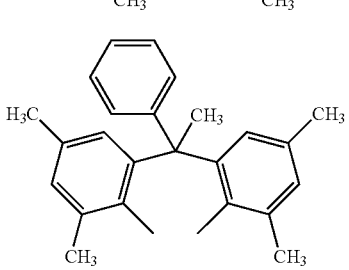
(A-22)

-continued
(A-23) 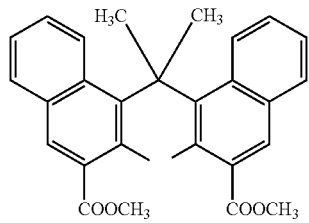
(A-24) 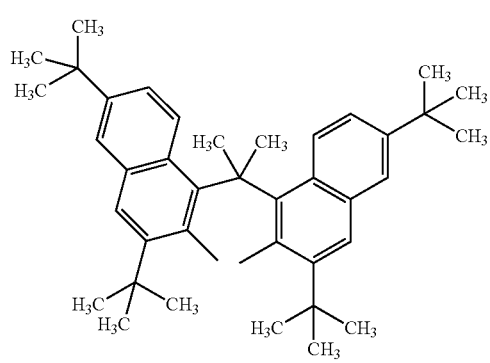
(A-25) 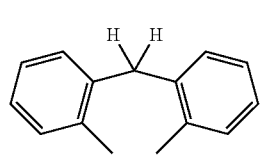
(A-26) 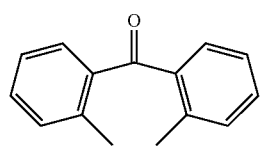
(A-27) 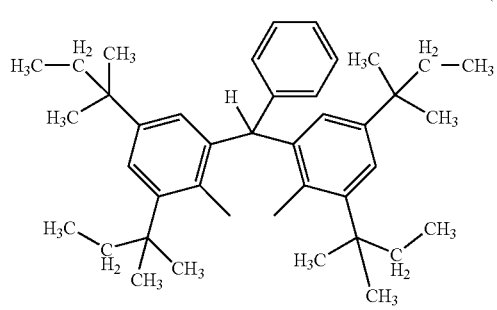
(A-28) 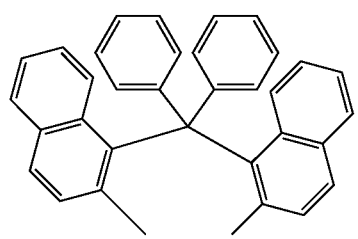
-continued
(A-29) 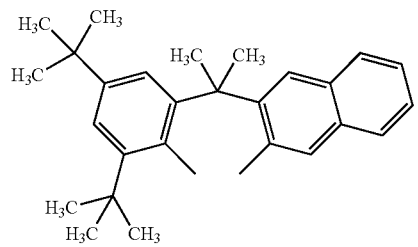
(A-30) 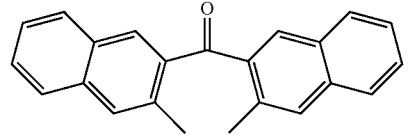
(A-31) 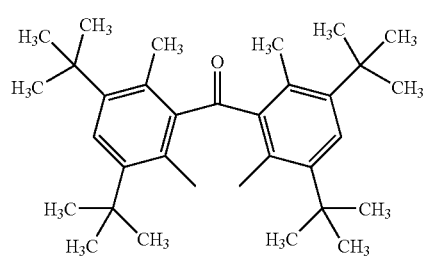
(A-32) 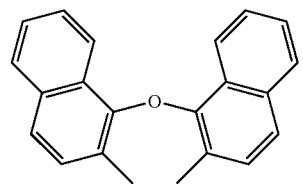
(A-33) 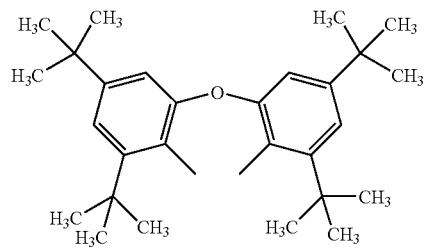
(A-34) 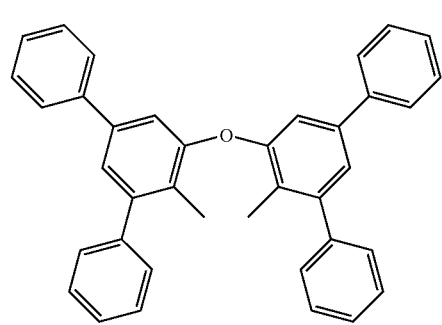

-continued

As mentioned above, the phosphite compounds as expressed by the above formulae (I) to (IV) include phosphites having various structures depending on combinations of substituents. Among them, preferable examples of the phosphite of the formula (I) include phosphites expressed by the following formulae (L-1) to (L-5), preferable examples of the phosphite of the formula (II) include phosphites expressed by the following formulae (L-6) to (L-32), preferable examples of the phosphite of the formula (III) include phosphites expressed by the following formulae (L-33) to (L-46) and (L-57), and preferable examples of the phosphite of the formula (IV) include phosphites expressed by the following formulae (L-47) to (L-57).

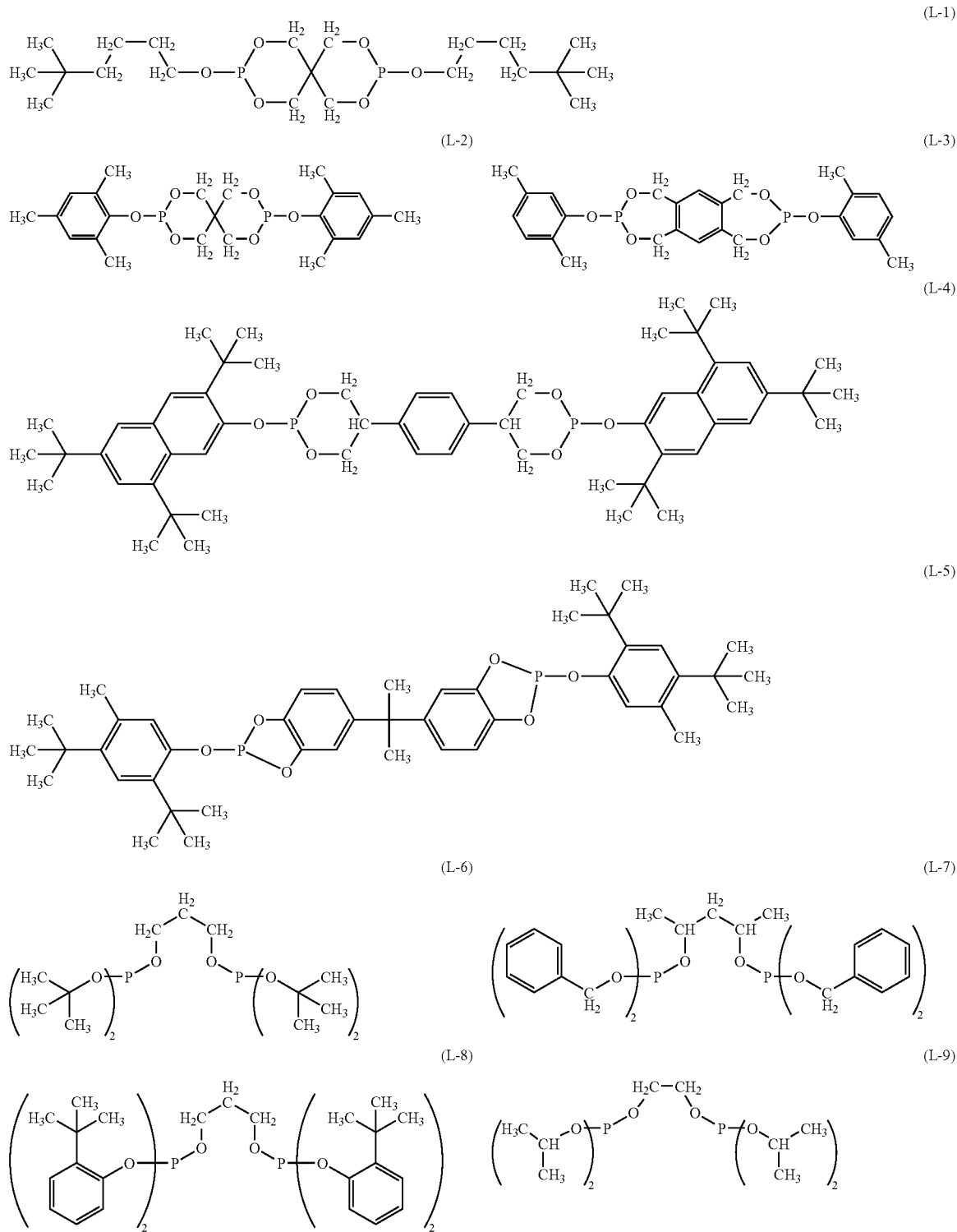

-continued
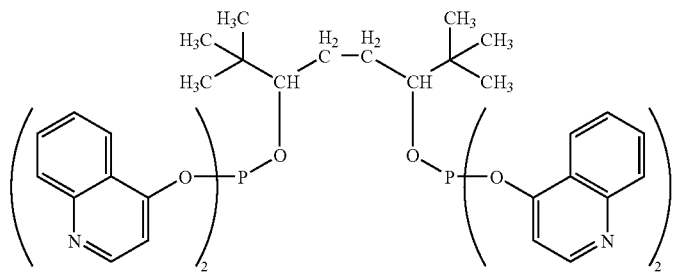
(L-10)
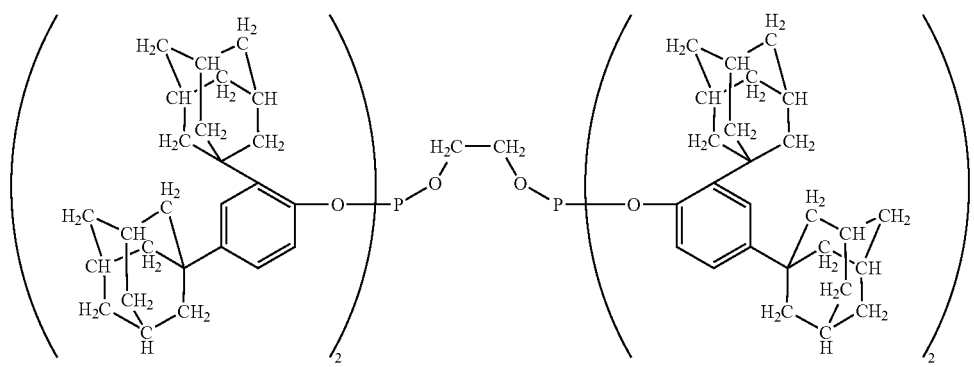
(L-11)
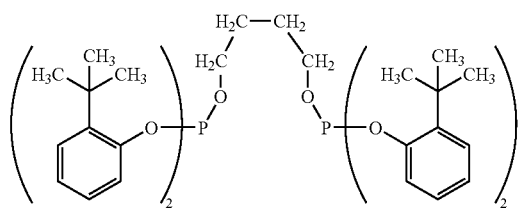
(L-12)
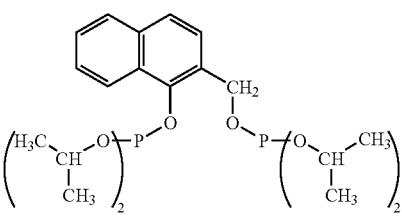
(L-13)
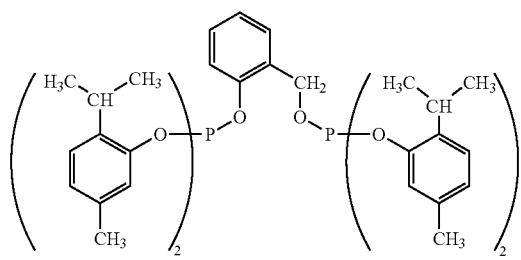
(L-14)
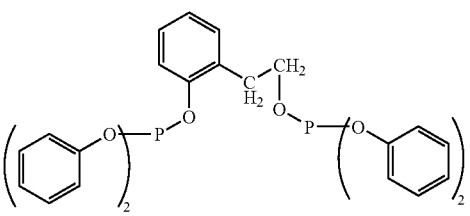
(L-15)
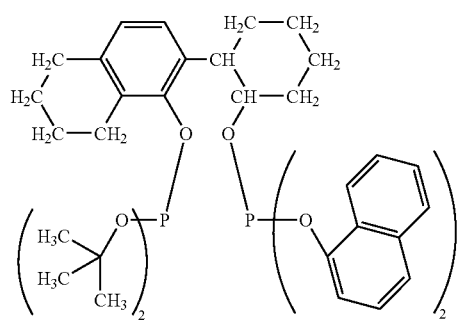
(L-16)

-continued
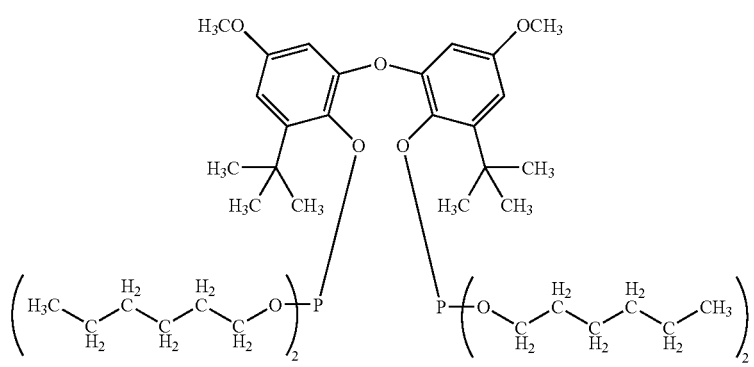
(L-17)
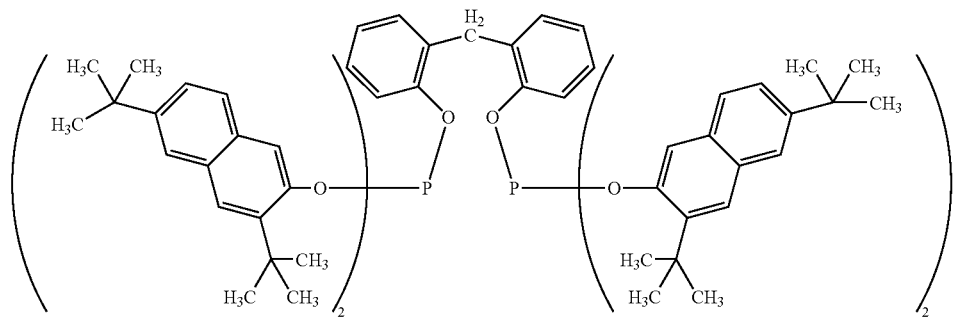
(L-18)
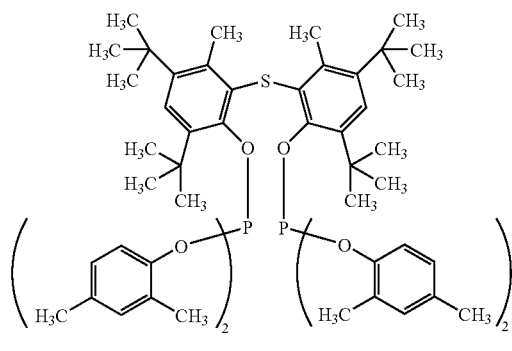
(L-19)
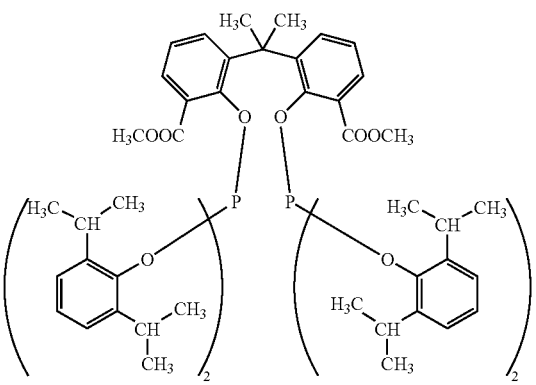
(L-20)
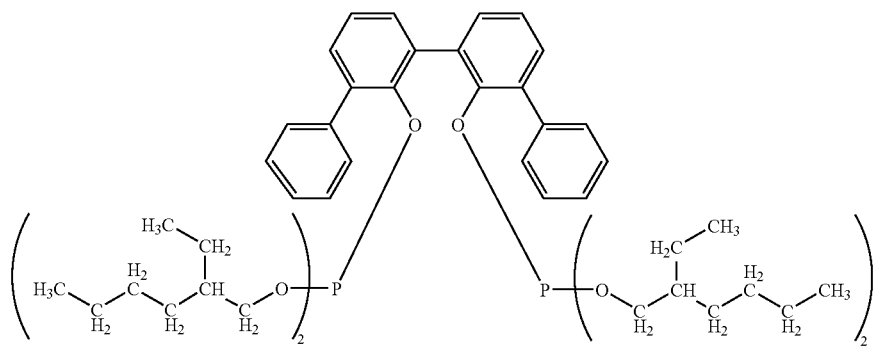
(L-21)

-continued
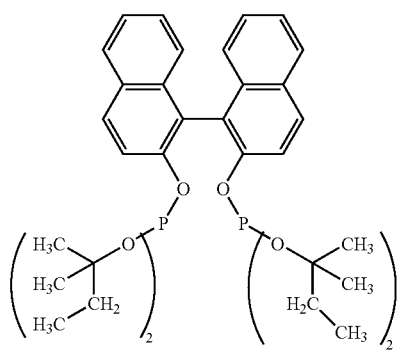
(L-22)
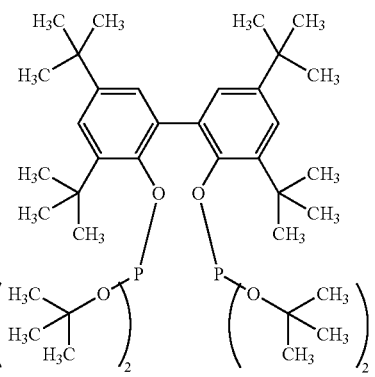
(L-23)
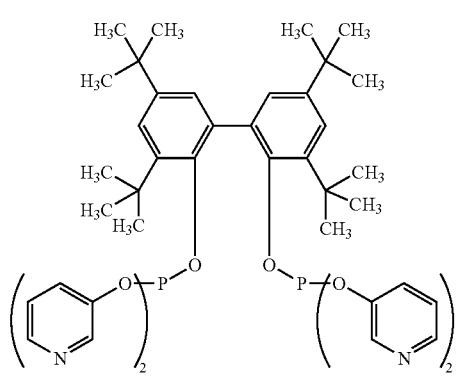
(L-24)
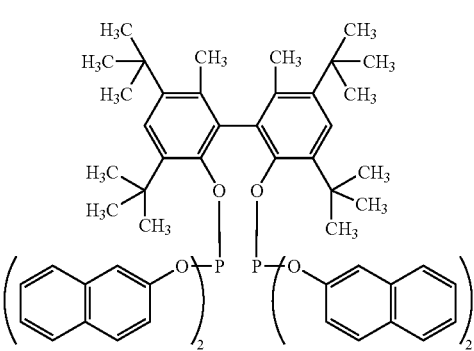
(L-25)
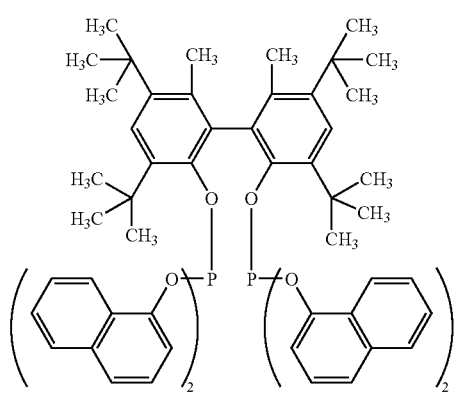
(L-26)
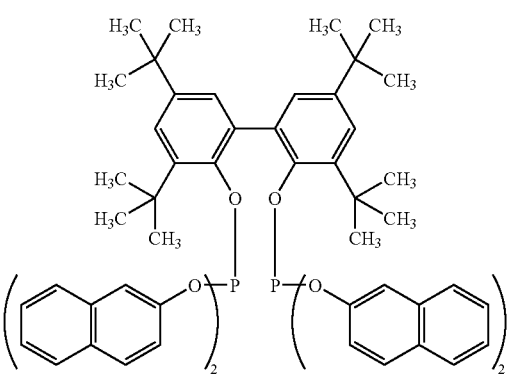
(L-27)
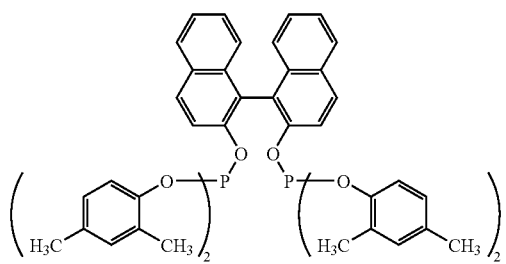
(L-28)
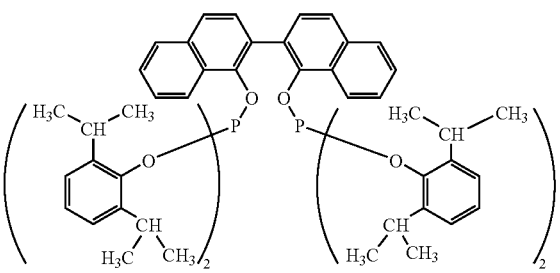
(L-29)

-continued
(L-30) 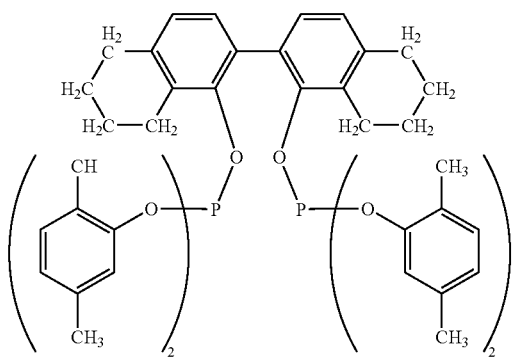
(L-31) 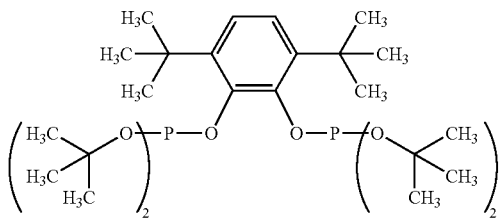
(L-32) 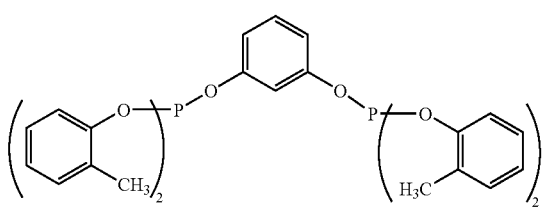
(L-33) 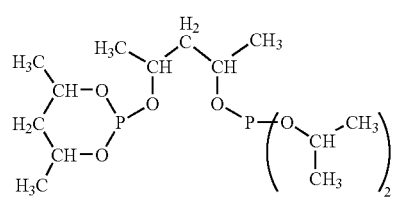
(L-34) 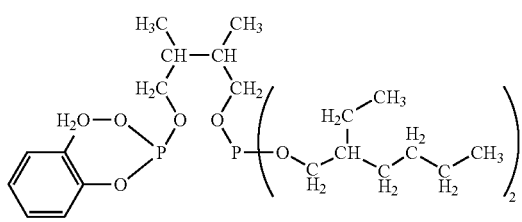
(L-35) 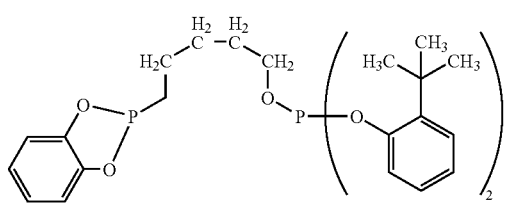
(L-36) 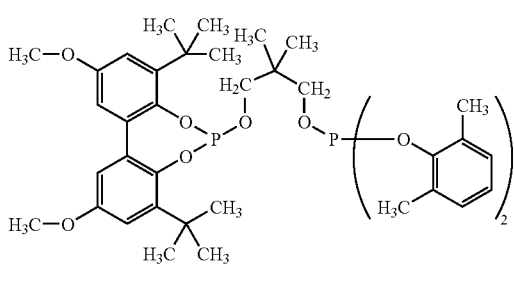
(L-37) 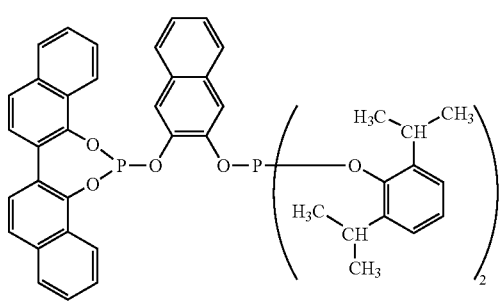
(L-38) 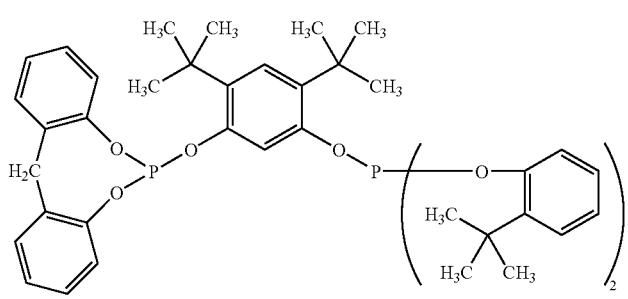

-continued
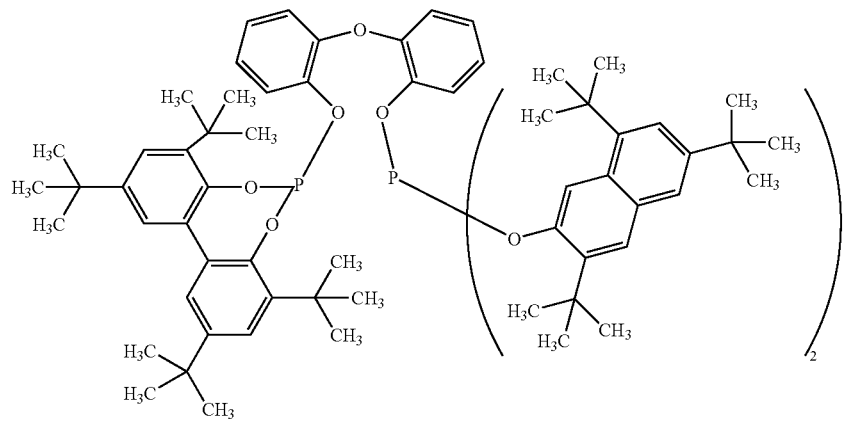
(L-39)
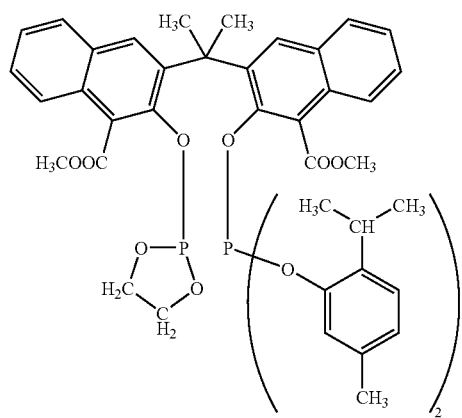
(L-40)
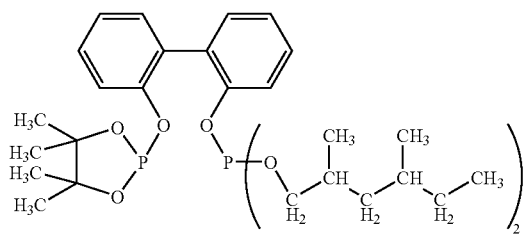
(L-41)
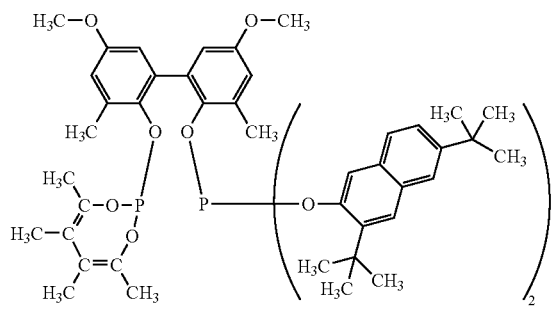
(L-42)
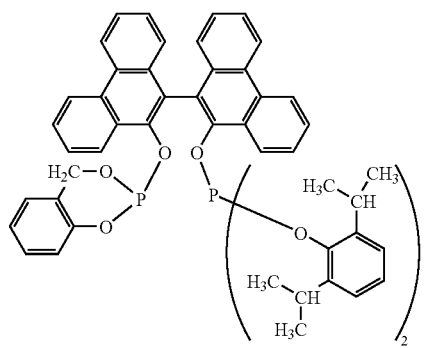
(L-43)
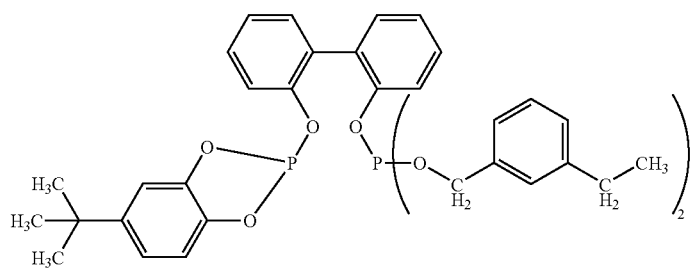
(L-44)

-continued
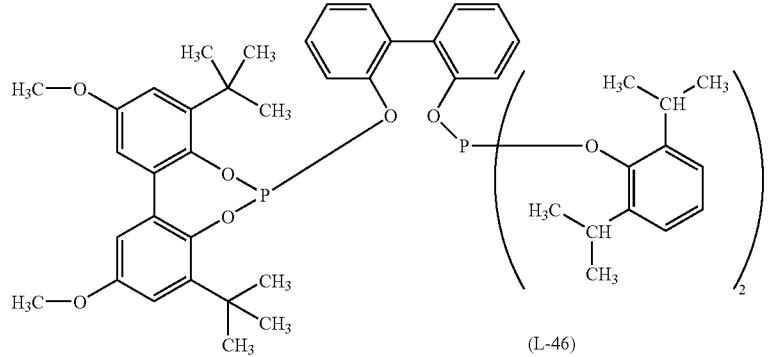
(L-45)
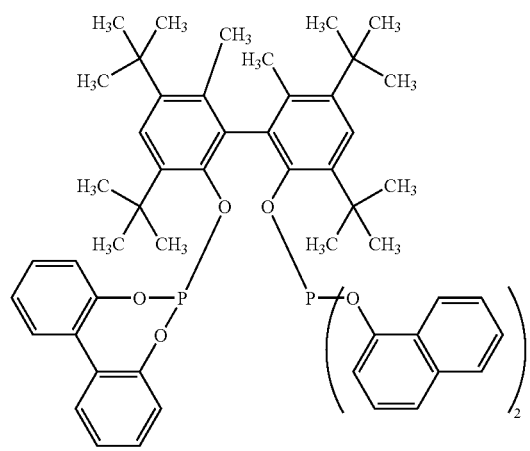
(L-46)
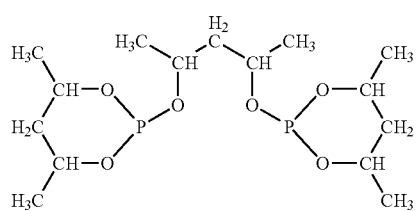
(L-47)
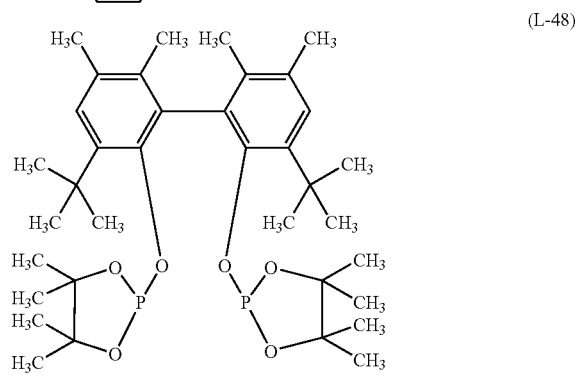
(L-48)
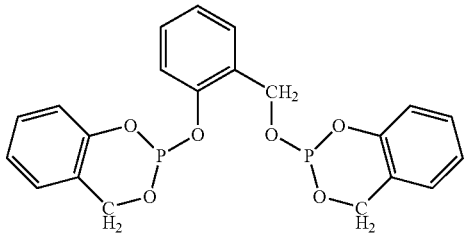
(L-49)
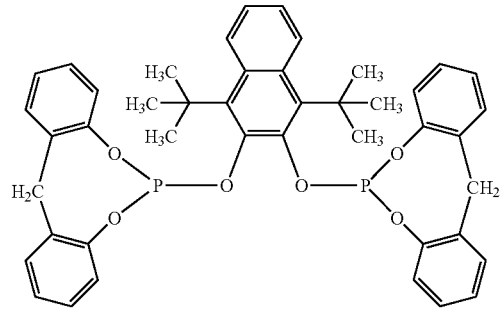
(L-50)
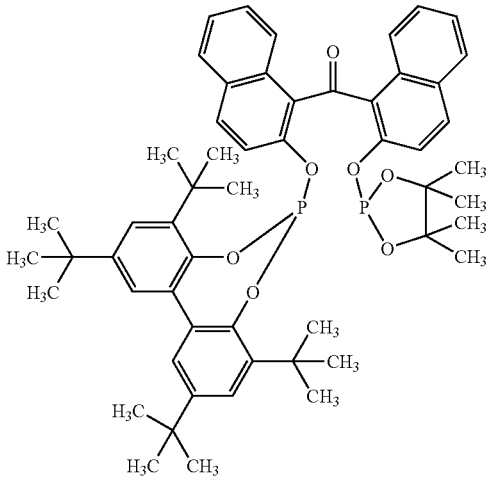
(L-51)

-continued
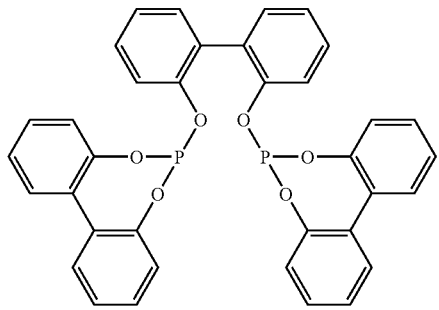
(L-52)
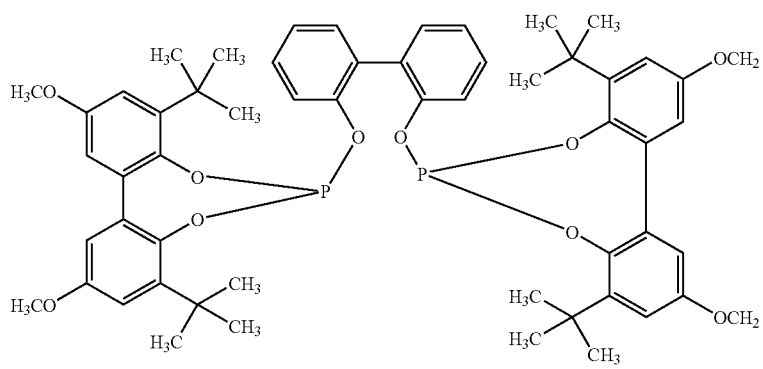
(L-53)
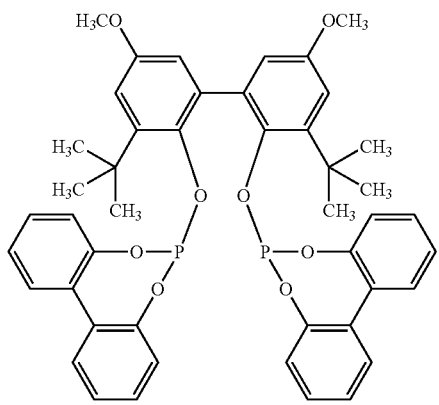
(L-54)
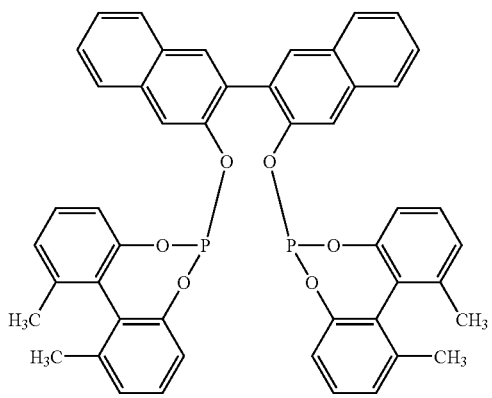
(L-55)
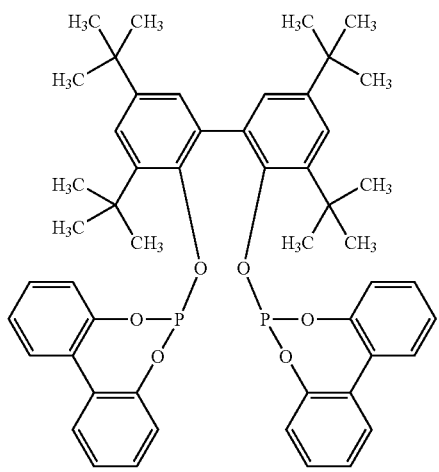
(L-56)
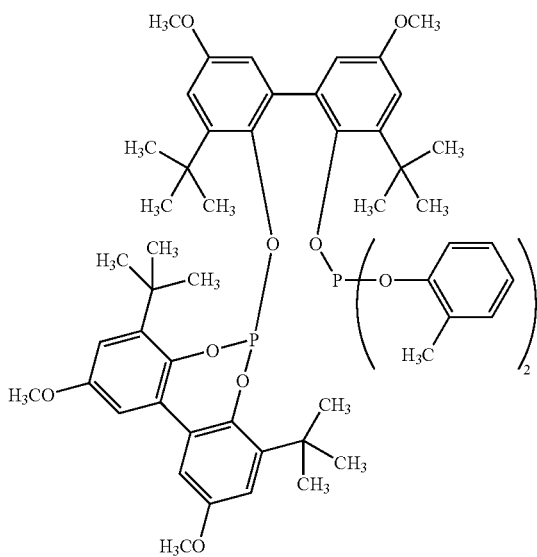
(L-57)

Among the above illustrated phosphite compounds, bidentate phosphite compounds having such structures as expressed by the formulae (II) to (IV) are preferable. Their examples include compounds having such structures as expressed by the above formulae (L-6) to (L-56). In order to improve stability of these phosphite compounds, $R^{10}$ to $R^{17}$ are preferably respectively independently an unsubstituted or substituted aryl group, $Z^1$ to $Z^3$ are preferably respectively independently an unsubstituted or substituted diarylene group, and $A^1$ to $A^3$ are preferably respectively independently an alkylene group, an arylene group, and an alkylene-arylene group or a diarylene group, which may have a substituent. Their typical examples include compounds having such structures as expressed by the above formulae (L-8), (L-10)to (L-12), (L-14), (L-15), (L-18) to (L-20), (L-24) to (L-30), (L-32), (L-36) to (L-39), (L-45), (L-46), (L-50) and (L-52) to (L-57).

The above multidentate coordinated phosphite compound is used in an amount of a mol ratio of usually at least 0.1, preferably at least 0.5, more preferably at least 1.0, and usually at most 10,000, preferably at most 500, more preferably at most 100, to the above-mentioned transition metal compound.

The above transition metal compound and the multidentate coordinated phosphite compound may be added to the reaction system respectively alone, or may be previously complexed to be used. Alternatively, the above multidentate coordinated phosphite compound may be bonded to some insoluble resin carriers, and the above transition metal compound may be carried thereon to form an insoluble solid catalyst to be used for the reaction. Further, only one kind of the multidentate coordinated phosphite compound may be used for the reaction, or an optional combination of at least two kinds of the multidentate coordinated phosphite compounds may be used at the same time for the reaction.

By reacting an allyl starting material compound and an oxygen nucleophilic agent in the presence of a catalyst comprising the above explained transition metal compound and multidentate coordinated phosphite compound, a new allyl compound (such as ether compounds or ester compounds) can be efficiently produced.

The reaction of the production method of the present invention is usually carried out in liquid phase. The reaction can be carried out either in the presence or absence of a solvent. When using a solvent, any optional solvent is usable so long as it dissolves the catalyst and the starting material compound and does not adversely affect the catalyst activity, and the kind of the solvent is not specially limited. Preferable examples of the solvent include carboxylic acids such as acetic acid, propionic acid or butyric acid, alcohols such as methanol, n-butanol or 2-ethylhexanol, ethers such as diglyme, diphenyl ether, dibenzyl ether, diallyl ether, tetrahydrofuran (THF) or dioxane, amides such as N-methyl-2-pyrolidone, dimethylformamide or dimethylacetamide, ketones such as cyclohexanone, esters such as butyl acetate, γ-butylolactone or di(n-octyl) phthalate, aromatic hydrocarbons such as toluene, xylene or dodecylbenzene, aliphatic hydrocarbons such as pentane, hexane, heptane or octane, a high boiling point material formed as a by-product in the allylation reaction system, and an allyl compound as a starting material, an allyl compound as a product, a compound derived from an eliminated group of a starting material allyl compound and the like. An amount of these solvents is not specially limited, but is usually at least 0.1 weight time, preferably at least 0.2 weight time, and usually at most 20 weight times, preferably at most 10 weight times, to a total amount of the allyl compound used as the starting material.

The actual reaction may be carried out by employing various reaction systems. For example, the reaction can be carried out in any of continuous system, semi-continuous system or batch wise system by using a stirring type completely mixing reactor, a plug flow type reactor, a solid bed type reactor, a suspension bed type reactor or the like.

When actually carrying out the reaction, reaction conditions may be optionally selected depending on a reaction substrate or a product. For example, when employing a stirring type completely mixing reactor, the reaction is carried out by a process comprising adding a catalyst solution prepared in a catalyst-preparing tank to a mixture solution of an allyl starting material compound, an oxygen nucleophilic agent and an optionally a solvent, introducing the resultant mixture into the reactor continuously or semi-continuously, retaining the reaction mixture at a reaction temperature with stirring to proceed the allylation reaction of the oxygen nucleophilic agent, and withdrawing a part of the reaction solution continuously or semi-continuously from the reactor. Also, when employing a plug flow type reactor, the reaction is carried out by passing the reaction solution containing the above starting materials and the catalyst through a tubular reactor maintained at a certain reaction temperature. This system is suitable for achieving a high conversion of the starting materials. Further, when employing an insoluble solid catalyst having a catalyst carried thereon, it is suitable to use a solid bed reaction system wherein the reaction is carried out by passing a solution containing starting materials through the reactor having the catalyst loaded, or it is possible to use a suspension bed reaction system wherein the reaction is carried out by stirring and mixing a solution containing starting materials and a particulate insoluble catalyst in a reactor and maintaining the reaction solution in suspension state.

The reaction temperature is not specially limited so long as it is a temperature at which the catalytic reaction proceeds, but when using a noble metal compound such as palladium, the reaction temperature should not be too high. If the reaction temperature is too high, there is a risk that metallization occurs and an effective catalyst concentration is reduced. Also, if the reaction temperature is too high, there is a risk that the phosphite compound is decomposed. Accordingly, a suitable reaction temperature is usually at least 0° C., preferably at least 20° C., more preferably at least 50° C., and usually at most 180° C., preferably at most 160° C., and more preferably at most 150° C.

The atmosphere in a reactor is preferably filled with a gas inert to the reaction system such as argon or nitrogen, in addition to vapors derived from a solvent, a starting material compound, a reaction product, a reaction by-product, a decomposed material of catalyst and the like. Particularly, it is necessary to pay a special attention so that the atmosphere should not be mixed with oxygen for example by air leakage. If the atmosphere is contaminated with oxygen, the catalyst is degraded and the phosphite compound is decomposed by oxidation. Thus, it is quite necessary to avoid the contamination of the atmosphere with oxygen.

The retention time of the reaction solution in the reactor, i.e. the reaction time, is varied depending on an aimed conversion value of the starting material, but it is necessary to prolong the reaction time if a higher conversion is desired under a constant catalyst concentration. On the other hand, if it is desired to reduce the reaction time by maintaining the high conversion, it is necessary to raise a catalyst activity by raising a catalyst concentration, increasing a catalyst amount or raising the reaction temperature. However, in order to avoid degradation of the catalyst or a side reaction by heat history, it is preferable not to employ unnecessarily long reaction time or high temperature.

In this case, it is preferable for improving a reaction activity to have a phosphonium compound and/or an ammonium compound present in the reaction system.

The phosphonium compound and/or the ammonium compound used in the present invention are not specially limited so long as they have basically a structure wherein four substituents are bonded to a phosphorus atom or a nitrogen atom. By providing such a structure, there is provided a counter cation forming only an ion pair milder than an alkali metal ion which is often conventionally used, and accordingly an attacking property, i.e. reactivity, of a nucleophilic agent can be raised. This is because in the case of an alkali metal ion, +1 valent charge is concentrated on the surface of a small alkali metal ion, whereas in the case of a phosphonium compound or an ammonium compound, the whole molecule is +1 valent and a phosphorus atom or a nitrogen atom having charges concentrated thereon is concealed by four substituents.

Hereinafter, an explanation is made with regard to each compound.

Phosphonium Compound

A phosphonium compound is not specially limited, provided that it is stable under reaction conditions and is solved in the reaction system and does not poison the catalyst (examples of a compound poisoning a catalyst include a compound containing a conjugated diene, a compound oxidizing or decomposing a phosphite compound such as a peroxide, and the like). In view of its solubility in the reaction system, the phosphonium compound has a molecular weight of usually at most 3,000, preferably at most 2,000, more preferably at most 1,500, and usually at least 40, preferably at least 70, more preferably at least 100.

Among them, a phosphonium compound having a structure expressed by the following formula (1) is preferable.

$$PX^1X^2X^3X^4 \quad (1)$$

In the above formula (1), $X^1$ to $X^4$ are respectively independently a hydrogen atom, a halogen atom, a hydroxyl group, an amino group, a chain-like or cyclic alkyl group, an aryl group (in the present specification, "aryl group" includes a heterocyclic compound forming an aromatic 6π electron cloud at the upper and lower parts of the ring), an alkoxy group, an aryloxy group, an alkylthio group or an arylthio group. The above illustrated groups may further have a substituent. The substituent is not specially limited so long as it does not adversely affect the reaction system, and preferable examples of the substituent include a halogen atom, a hydroxyl group, an amino group, a chain-like or cyclic alkyl group, an aryl group, an alkoxy group, an aryloxy group, an alkylthio group or an arylthio group. When the above illustrated unsubstituted or substituted groups contain a carbon chain, the carbon chain may have at least one carbon-carbon double bond or triple bond.

The carbon number of $X^1$ to $X^4$ are respectively independently usually at most 40, preferably at most 30, more preferably at most 20. At least two optional groups of $X^1$ to $X^4$ may be bonded to each other to form at least one cyclic structure. The number of cycles is not specially limited, but is usually 0 to 3, preferably 0 to 2, more preferably 0 or 1. When at least two groups of $X^1$ to $X^4$ are bonded to form a cyclic structure, its carbon number is usually at most 40×p, preferably at most 30×p, more preferably at most 20×p, wherein p is the number of groups participating in the formation of a cyclic structure. Also, the number of atoms forming each ring is not specially limited, but is usually 3 to 10-membered ring, preferably 4 to 9-membered ring, more preferably from 5 to 7-membered ring. When a plurality of rings are present, these rings may be partly jointly owned to form a condensed ring structure.

Among the above illustrated groups, preferable examples of $X^1$ to $X^4$ are respectively independently a hydrogen atom, a substituted or unsubstituted chain-like or cyclic alkyl-group, an aryl group, an alkoxy group, an arylalkoxy group or an aryloxy group, and more preferable examples include a substituted or unsubstituted chain-like or cyclic alkyl group or an aryl group (in this case also, at least two optional groups of the alkyl group or the aryl group of $X^1$ to $X^4$ may be bonded to form at least one cyclic structure as mentioned above).

Particularly, at least one group of $X^1$ to $X^4$ is preferably a group capable of dispersing +1 valent charge on the phosphorus atom of a phosphonium compound by resonance effect. The phosphonium compound having such a group can provide a counter cation for forming an ion pair. Examples of a group capable of providing such resonance stabilization of cation include a substituted or unsubstituted aryl or a vinyl group, typical example of which include a phenyl group, a 4-methoxyphenyl group, 4-t-butylphenyl group, a 2,4-di-t-butylphenyl group, a 2,4-di-t-butyl-6-methylphenyl group, a 2,5-dimethylphenyl group, a 2,4,6-trimethoxyphenyl group, a 1-naphthyl group, a 2-naphthyl group, a 1-methyl-2-naphthyl group, a vinyl group or a 1-butenyl group. Among them, when taking a strength of effect of resonance stabilization or easy synthesis of a phosphonium compound into consideration, a substituted or unsubstituted aryl group is particularly preferable.

Examples of the phosphonium compound usable in the present invention include hydroxytrimethoxyphosphonium, hydroxymethoxydimethylphosphonium, chlorohydroxydicyclohexylphosphonium, bromotriethoxyphosphonium, trichloro-3-phenoxy-1-propenylphosphonium, dichlorohydroxyphenylphosphonium, tri(t-butoxy)cyclohexylphosphonium, fluorotris(4-methoxyphenyl)phosphonium, methyltri(phenoxy)phosphonium, dimethylaminotris(4-ethylphenyl)phosphonium, tri(ethylthio)hydroxyphosphonium, diethoxyethylphenylthiophosphonium, trifluoromethyltris(dimethylamino)phosphonium, tetra(t-butyl)phosphonium, trimethyl-1-propynylphosphonium, and the like.

Among them, in view of stability and solubility, preferable examples include phosphonium compounds having respectively independently a hydrogen atom, a substituted or unsubstituted chain-like or cyclic alkyl group, an aryl group, an alkoxy group, an arylalkoxy group, an aryloxy group or an alkylaryloxy group as $X^1$ to $X^4$. Typical examples of such phosphonium compounds include tetra(n-dodecyl)phosphonium, tetrakis(2-octenyl)phosphonium, cyclohexyltris(2-methyl-2-butenyl)phosphonium, methoxymethyldi(n-butyl)phosphonium, allyl-t-butylethylphenoxyphosphonium, 4-acetoxy-2-butenylphenylbis(2,4-di-t-butylphenoxy)phosphonium, t-butoxy-3-bromo-1-naphthoxybis(4-nitrophenyl)phosphonium, di(1-naphthoxy)-2,4-di-t-butyl-5-methylphenoxy-2-acetoxy-3-butenylphosphonium, 2-butene-1,4-bis(tris(2-methoxyphenoxy)phosphonium), tetrakis(2,4,6-trimethoxyphenoxy)phosphonium, and the like.

Further, more preferable examples of a phosphonium compound include a compound having a chain-like or cyclic and substituted or unsubstituted alkyl or aryl group as $X^1$ to $X^4$. These preferable examples include a phosphonium compound having a structure wherein all of the four substituents $X^1$ to $X^4$ of the phosphonium compound are bonded to a phosphorus atom by P—C bond. Examples of such a phosphonium compound include tetramethylphosphonium, tetra(n-butyl)phosphonium, tetra(methylol)phosphonium, 4-acetoxybutyldiethyl-2-methoxyethylphosphonium, neopentyltriphenylphosphonium, tetraphenylphosphonium, tetrakis(4-fluorofluorophenyl)phosphonium, 2-butenylbis(4-t-butylphenyl)-3-cyanopropylphosphonium, methyltriphenylphosphonium, 4-methylcyclohexyltri(i-propyl)phosphonium, dimethylpentamethylenephosphonium, 4-acetoxy-2-butenyltriphenylphosphonium, 2-butenyl-1,4-bis(triphenylphosphonium), naphthalene-1,8-bis(trimethylphosphonium), biphenyl-2,2'-bis(diphenylmethylphosphonium), and the like. Also, the examples include all of a phosphonium compound having an allyl group derived from reaction of phosphine and an allyl compound.

Particularly preferable examples include a phosphonium compound wherein at least one of $X^1$ to $X^4$ is a group capable of dispersing +1 valent charge on a phosphorus atom-by resonance effect, as mentioned above. Examples of such a preferable phosphonium compound include trimethylphenylphosphonium, 4-acetoxy-2-butenyldicyclohexylphenylphosphonium, 2-butenyl-1,4-bis(dicyclohexylphenylphosphonium), triethyl-1-naphthylphosphonium, tri-n-butyl-1-methyl-2-naphthylphosphonium, diethylphosphinedrium, 4-acetoxy-2-butenyldiphenyl-i-propylphosphonium, 2-butenyl-1,4-bis(diphenyl-i-propylphosphonium), dimethylbis(2,4-dimethylphenyl)phosphonium, t-butyl-1-acetoxymethyl-2-propenylbis(2-naphthyl)phosphonium, diphenylisophosphinedrium, methyltriphenylphosphonium, 4-acetoxy-2-butenyltriphenylphosphonium, 2-butenyl-1,4-bis(triphenylphosphonium), 1-butene-3,4-bis(triphenylphosphonium), 1-acetoxymethyl-2-propenyltris(4-methoxydiphenyl)phosphonium, tetraphenylphosphonium, di(1-naphthyl)diphenylphosphonium, tetrakis(2-naphthyl)phosphonium, naphthalene-2,6-bis(triphenylphosphonium), and the like.

Further, in order to further weaken cationic property of phosphonium, it is preferable that such an aryl group has an electron donative substituent such as an alkyl group or a methoxy group.

When the above-mentioned phosphonium compound is present in the reaction system of carrying out allylation reaction, an effect of improving a reactivity is achieved. In this case, any one kind of phosphonium compound may be used alone or several kinds of phosphonium compounds may be used by optionally combining and mixing.

A method for introducing the phosphonium compound into the reaction system is not specially limited, but there is a method of positively adding the phosphonium compound to the reaction system or a method of preparing the phosphonium compound in the reaction system. These methods are further explained hereinafter by referring to examples.

First, the method of positively adding the phosphonium compound to the reaction system is a method of feeding the phosphonium compound together with an allyl compound, a nucleophilic agent, a catalyst, a reaction medium and the like to a reactor, and the phosphonium compound may be a new phosphonium compound or a phosphonium compound recycled from the reaction process. In connection with this, it should be noted that since a commercially available phosphonium compound is generally charged with +1 valent charge per one phosphorus atom, it is in a form of salt with its corresponding counter anion, but the counter anion corresponding to phosphonium is preferably a nucleophilic agent reactive with an allyl starting material compound in the reaction system. If the counter anion is not a nucleophilic agent but a phosphonium compound in a form of salt with other counter anion is added, it is desired that the other counter anion does not poison a catalyst and is decomposed by reacting with an allyl compound in the reaction system so that a nucleophilic agent becomes newly a counter anion. Generally known examples of a counter anion of a commercially available phosphonium compound include a halogen atom ion such as chloride, bromide or iodide, and hexafluorophosphate, hexachlorophosphate, hydrogen sulfate, tetrachloroborate, trifluoromethanesulfonate, perchlorate or the like. Among these examples, it is generally considered that there is a high possibility that a halide ion poisons a transition metal catalyst. When using such a halide phosphonium compound, it is preferable to previously remove a halide ion by anion exchange reaction. In this case, it is more preferable to make a nucleophilic agent using a new counter anion in the allylation reaction.

On the other hand, the method of preparing a phosphonium compound in the reaction system includes a method of adding a trivalent phosphorus compound as a starting material for phosphonium. This method uses such a reaction as described in the J. Am. Chem. Soc., 1992, 114, p 6858, and this reaction comprises nucleophilicly attacking a terminal allyl carbon of a π-allyl complex of transition metal by a trivalent phosphorus compound to form a phosphonium compound having an allyl group newly bonded. Actually, when a production process of 1,4-diacetoxy-2-butene by reaction of 3,4-diacetoxy-1-butene as an allyl starting material compound and acetoxide as a nucleophilic agent in the presence of triphenylphosphine in an amount of 200 equivalents to palladium and palladium-bidentate coordinated phosphite catalyst is analyzed by $^{31}$P-NMR spectrum, a signal of triphenylphosphine of –6 ppm rapidly disappears at the initial stage of reaction and is converted to signals of a plurality of phosphoniums observed at 17 to 25 ppm. Judging from the chemical shift values, these signals are considered to be due to phosphoniums, and the reason why a plurality of kinds are observed, is due to the formation of isomers such as
[PPh$_3$(CH$_2$CH=CHCH$_2$OAc)]$^+$[OAc]$^-$,
[PPh$_3$CH(CH$_2$OAc)(CH=CH$_2$)]$^+$[OAc]$^-$,
[PPh$_3$(CH$_2$CH=CHCH$_2$)PPh$_3$]$^{2+}$2[OAc]$^-$,
[PPh$_3$CH(CH$_2$PPh$_3$)(CH=CH$_2$)]$^{2+}$2[OAc]$^-$, or the like.

When carrying out such a process, it should be noted that a ligand coordinated to a transition metal compound is eliminated and a catalyst activity is lowered when a coordination power of a trivalent phosphorus compound added as a starting material for phosphonium to a transition metal compound is too high. In such a case, it is necessary to previously convert into a phosphonium compound at the outside of the system before feeding or to wait for slowly converting into a phosphonium compound during carrying out the process.

In view of economic conditions, it is advantageous to use the above phosphonium compound in a small amount. Thus, the phosphonium compound is used to a metal compound as an allylation catalyst (fully described above) at a mol ratio of usually at least 0.1, preferably at least 1, more preferably at least 5, further preferably at least 10, most preferably at least 15, and usually at most 10,000, preferably at most 5,000, more preferably at most 1,000, most preferably at most 500.

Ammonium Compound

An ammonium compound usable in the present invention basically has a structure having four substituents bonded to nitrogen. Usually, the usable ammonium compound is not specially limited so long as it is stable under the reaction conditions and soluble in the reaction system and does not poison a catalyst (examples of a compound poisoning the catalyst include a compound containing a conjugated diene, a compound oxidizing and decomposing a phosphite compound such as a compound containing peroxide, and the like). In view of its solubility in the reaction system, the ammonium compound has a molecular weight usually at most 3,000, preferably at most 2,000, more preferably at most 1,000, and usually at least 20, preferably at least 40, more preferably at least 60.

Among them, an ammonium compound having a structure expressed by the following formula (2) is preferable.

$$NX^1X^2X^3X^4 \quad (2)$$

In the above formula (2), $X^1$ to $X^4$ are respectively independently a hydrogen atom, a halogen atom, a hydroxyl group, an amino group, a chain-like or cyclic alkyl group, an aryl group (in the present specification, "aryl group" includes a heterocyclic compound forming an aromatic $6\pi$ electron cloud at the upper and lower parts of the ring), an alkoxy group, an aryloxy group, an alkylthio group or an arylthio group. The above illustrated groups may further have a substituent. The substituent is not specially limited so long as it does not adversely affect the reaction system, and preferable examples of the substituent include a halogen atom, a hydroxyl group, an amino group, a chain-like or cyclic alkyl group, an aryl group, an alkoxy group, an aryloxy group, an alkylthio group or an arylthio group. When the above illustrated unsubstituted or substituted groups contain a carbon chain, the carbon chain may have at least one carbon-carbon double bond or triple bond.

The carbon number of $X^1$ to $X^4$ are respectively independently usually at most 40, preferably at most 30, more preferably at most 20. At least two optional groups of $X^1$ to $X^4$ may be bonded to each other to form at least one cyclic structure. The number of cycles is not specially limited, but is usually 0 to 3, preferably 0 to 2, more preferably 0 or 1. When at least two groups of $X^1$ to $X^4$ are bonded to form a cyclic structure, its carbon number is usually at most 40×p, preferably at most 30×p, more preferably at most 20×p, wherein p is the number of groups participating in the formation of a cyclic structure. Also, the number of atoms forming each ring is not specially limited, but is usually 3 to 10-membered ring, preferably 4 to 9-membered ring, more preferably from 5 to 7-membered ring. When a plurality of rings are present, these rings may be partly jointly owned to form a condensed ring structure.

Among the above illustrated groups, preferable examples of $X^1$ to $X^4$ are respectively independently a hydrogen atom, a substituted or unsubstituted chain-like or cyclic alkyl group, an aryl group, an alkoxy group, an arylalkoxy group, an aryloxy group or an alkylaryloxy group, and more preferable examples include a substituted or unsubstituted chain-like or cyclic alkyl group or an aryl group (in this case also, at least two optional groups of the alkyl group or the aryl group of $X^1$ to $X^4$ may be bonded to form at least one cyclic structure).

Further, the ammonium compound expressed by the above formula (2) include a compound having an N=C double bond such as N-substituted pyridine, N-substituted oxazolium, N-substituted thiazolium, and the like. Still further, the above ammonium compound includes mono- or polyammonium compounds derived from polyamines such as bidentate chelate type diamines having an amino group as a substituent.

Examples of the ammonium compound usable in the present invention include trimethoxyammonium, methoxydimethyl ammonium, chlorohydroxydicyclohexyl ammonium, bromotriethyl ammonium, dimethylthiodiphenyl ammonium, tri(t-butyl)cyclohexyl ammonium, ethoxytris(4-methoxyphenyl) ammonium, methyltri(phenoxy)ammonium, dimethoxyacetyl ammonium, tri(ethylthio)isopropyl ammonium, diethoxyethylphenylthio ammonium, tetra(n-butyl)ammonium, triethylhydro ammonium, trimethyl-1-propynyl ammonium, N-t-butyl-5-methyloxazolium, 4-methoxypyridinium, N-phenylthiazolium, Et$_2$HN—CH$_2$—CH$_2$—NEt$_2$, Me$_2$HN—CH$_2$—CH$_2$—CH$_2$—NHMe$_2$, Me$_2$HN—CH$_2$—CH$_2$—NHMe$_2$, and the like. In the present specification, Me represents a methyl group and Et represents an ethyl group.

However, generally, compounds easily available and suitably usable in the present invention include the following two types of compounds.

(i) Compounds wherein one of $X^1$ to $X^4$ is a hydrogen atom, and the other three groups are respectively independently a substituted or unsubstituted alkyl or aryl group (at least two optional groups of these alkyl or aryl groups may be bonded to each other to form at least one cyclic structure).

(ii) Compounds wherein all of $X^1$ to $X^4$ are respectively independently a substituted or unsubstituted alkyl or aryl group (at least two optional groups of these alkyl or aryl groups may be bonded to each other to form at least one cyclic structure).

Examples of the above type (i) compound include triethyl ammonium, triisopropyl ammonium, tri-n-dodecyl ammonium, diethylisopropyl ammonium, ethyl-n-propyl-t-butyl ammonium, 3-chloro-1-propyldiphenyl ammonium, triallyl ammonium, geranylbis(4-methoxyphenyl)ammonium, tris (2,4-dimethylphenyl)ammonium, 3-fluorophenyl-2-methylphenyl-2-naphthyl ammonium, tri(2-naphthyl)ammonium, pyridinium, 4-t-butyl ammonium, 4-cyanopyridinium, and compounds expressed by the following formulae (N-1) to (N-6).

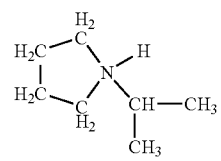
(N-1)

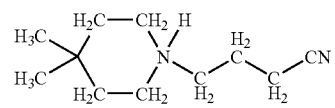
(N-2)

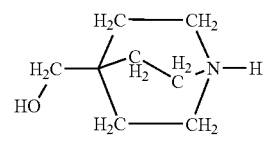
(N-3)

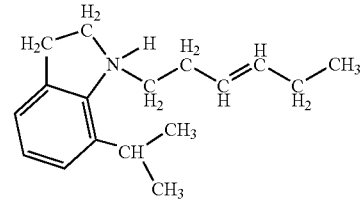
(N-4)

-continued

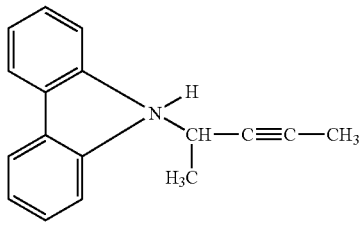 (N-5)

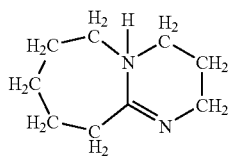 (N-6)

Examples of the above type (ii) compounds include tetramethyl ammonium, tetrabenzyl ammonium, tetraundecenyl ammonium, trimethylethyl ammonium, triallyl-3-pentynyl ammonium, triethylallyl ammonium, diphenylmethylethyl ammonium, trimethyl-2-butenyl ammonium, bis(4-methoxy-1-butyl)diethyl ammonium, di(1-naphthyl)diisopropyl ammonium, t-butylethylisopropyl-4-fluorophenyl ammonium, tris(4-ethylphenyl)-4-acetoxy-2-butenyl ammonium, and compounds expressed by the following formulae (N-7) to (N-12).

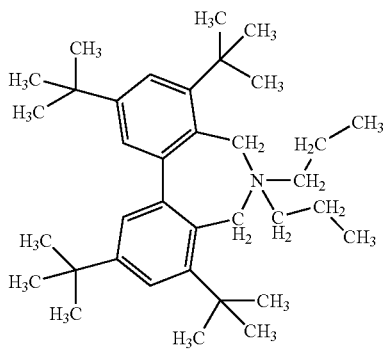 (N-7)

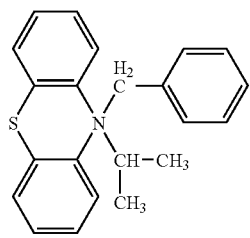 (N-8)

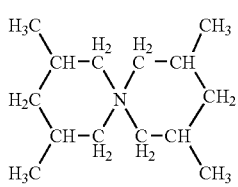 (N-9)

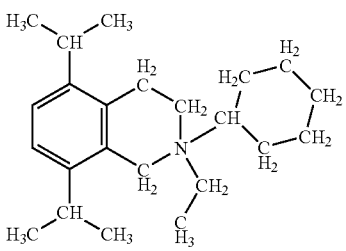 (N-10)

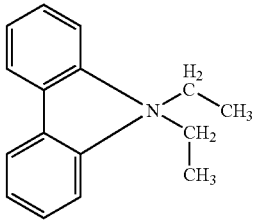 (N-11)

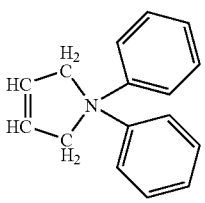 (N-12)

Among the above-mentioned type (i) and type (ii) compounds, an ammonium compound wherein $X^1$ to $X^4$ other than hydrogen are a substituted or unsubstituted alkyl or aryl group is preferable. Examples of such type (i) ammonium compounds include tri-n-octyl ammonium, tris(6-t-butyl-2-naphthyl)ammonium, di-n-propylethylmethyl ammonium, n-propyl-n-butyl-n-pentyl ammonium, 2-chloroethyl-3-methoxypropyl-4-trimethylsilylbutyl ammonium, and the like, and examples of such type (ii) ammonium compounds include tetra-n-nonyl ammonium, tetraphenyl ammonium, diethyldiisopropyl ammonium, triethylbenzyl ammonium, methylethyl-n-propyl-n-butyl ammonium, methyl-t-butyldi(1-naphthyl)ammonium, 5-bromopentyldiethylmethyl ammonium, tris(2,5-dimethylphenyl)-n-octyl ammonium, and the like.

Among the above type (i) and type (ii) ammonium compounds, type (i) ammonium compounds are more preferable from an economical viewpoint since the type (i) ammonium compounds can be easily prepared by acid-base reaction of an acidic material such as acetic acid or phenol and original tertiary amine excluding coordinate-bonded proton. Particularly, type (i) ammonium compounds wherein all of three alkyl groups other than proton are the same are preferable since their production cost is cheap. Examples of such an ammonium compound include an ammonium compound wherein proton is coordinate-bonded to a trialkylamine having the same alkyl groups, such as triethyl ammonium, tri-n-propyl ammonium, triisopropyl ammonium, tri-n-butyl ammonium, tri-sec-butyl ammonium, tri-n-pentyl ammonium, tri-n-neopentyl ammonium, tri-i-octyl ammonium, tri-n-octyl ammonium, tridecanyl ammonium, and the like. Further, an ammonium compound wherein proton is coordinate-bonded to 1,8-diazabicyclo[5.4.0]undecene-7 (DBU) is preferable.

The above-mentioned ammonium compounds achieve an effect of improving a reactivity when they are present in the reaction system of carrying out allylation reaction. In this case, any one kind of ammonium compound may be present alone, or a plurality of kinds of ammonium compounds may be mixed in optional combination.

A method for introducing an ammonium compound into the reaction system is not specially limited, but its examples include a method of positively adding the ammonium compound to the reaction system or a method of preparing the ammonium compound in the reaction system. These methods are further explained by giving concrete examples hereinafter.

First, the method of positively adding the ammonium compound to the reaction system is a method of feeding the ammonium compound together with an allyl compound, a nucleophilic agent, a catalyst, a reaction medium and the like into a reactor, and the ammonium compound may be a new ammonium compound or may be an ammonium compound recycled from the reaction process. In this regard, it should be noted that since a commercially available ammonium compound generally has +1 valent charge per one nitrogen, it takes a form of salt with its corresponding counter anion, but it is preferable that this counter anion corresponding to ammonium is a nucleophilic agent to be reacted with an allyl starting material compound in the reaction system. If the counter anion is not a nucleophilic agent and an ammonium compound in a form of a salt with other counter anion is added, it is desired that the other counter anion does not poison a catalyst and is decomposed by reaction with an allyl compound in the reaction system, and a nucleophilic agent newly becomes a counter anion. Generally known examples of a counter anion of a commercially available ammonium compound include a halide ion such as chloride, bromide or iodide, and hexafluorophosphate, hexachlorophosphate, hydrogen sulfate, tetrachloroborate, trifluoromethane sulfonate, perchlorate and the like. Among them, it is generally considered that there is a high possibility that the halide ion poisons a transition metal catalyst. When such a halogenated ammonium compound is used in the reaction, it is preferable to previously remove it by anionic change reaction or the like. In this case, it is more desirable that a new counter anion is used as a nucleophilic agent to be used for allylation reaction.

On the other hand, examples of the method of preparing an ammonium compound in the reaction system include a method of adding an amine or pyridine compound as a starting material for ammonium. In this method, these compounds showing a basic property causes acid-base reaction with a proton acidic site of a nucleophilic agent in a reactor, and as this result, an ammonium or pyridinium compound having a structure having proton coordinate-bonded to a non-covalent electron pair on nitrogen. When carrying out such a process, it should be noted that when a nucleophilic agent has a proton acidic site, this method can be satisfactorily carried out and achieves a substantial effect particularly in the reaction of an oxygen nucleophilic agent such as phenol or carboxylic acids and a carbon nucleophilic agent such as malonic acid ester derivatives, but when a nucleophilic agent is a nitrogen nucleophilic agent such as amines, a substantial effect can not be achieved since amines are originally basic. Further, it should be noted that when an amine compound added as a starting material for ammonium has an excessively high coordinative power to a transition metal compound, a ligand originally coordinated to a transition metal compound is eliminated and a catalyst activity is lowered. In such a case, it is necessary to previously convert an amine compound into an ammonium compound at the outside of the system before feeding or to wait that an amine compound is gradually converted into an ammonium compound during carrying out the process.

It is advantageous from an economical viewpoint that the above ammonium compound is used in a smaller amount. Thus, the ammonium compound is used in a mol ratio of usually at least 0.1, preferably at least 1, more preferably at least 5, further preferably at least 10, most preferably at least 15, and usually at most 10,000, preferably at most 5,000, more preferably at most 1,000, most preferably at most 500, to a metal compound as an allylation reaction catalyst as fully illustrated above.

Also, many separating operations used in a conventional liquid catalyst recycling process can be employed for separating a catalyst and an allyl compound obtained in the reaction. Examples of the separating operations include distillation operations such as simple distillation, vacuum distillation, thin film distillation, water vapor distillation or the like, and other separating operations such as gas-liquid separation, evaporation, gas stripping, gas absorption and extraction. The separating operation of each component may be carried out respectively in an independent step, or separation of two or more components may be carried out at the same time in a single step. When a part of an allyl starting material compound or an unreacted nucleophilic agent remains, they may be recovered by a separating method in the same manner as above and may be recycled into a reactor, which provides an economical advantage. Further, it is economically desirable to recycle the separated catalyst into the reactor as it is or to recover the separated catalyst to be reactivated for reuse.

In the production method of the above allyl compound, when using 3,4-disubstituted 1-butene of the above formula (b) or 1,4-disubstituted 2-butene of the above formula (c) as an allyl starting material compound and a difunctional oxygen nucleophilic agent as an oxygen nucleophilic agent, there is produced a novel condensation copolymer containing a butenediyl unit expressed by the following A and A' derived from the butene and a dioxy unit expressed by the following B, B' and/or B" derived from the difunctional oxygen nucleophilic agent.

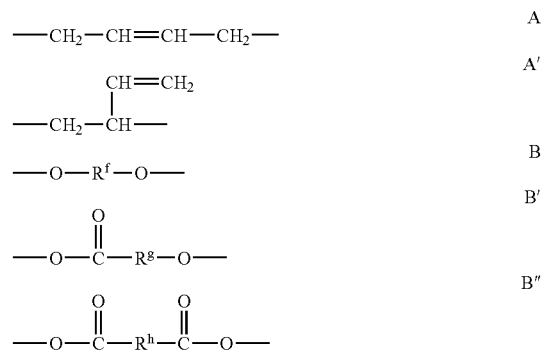

(In the above formulae, $R^f$, $R^g$ and $R^h$ are respectively independently a bivalent organic group which may have a substituent.)

In the copolymer, a mol ratio of the butenediyl unit expressed by A and the butenediyl unit expressed by A' is not specially limited, but there is a tendency that the amount of A becomes larger, and A:A' is usually at least 1:10, preferably at least 1:2, more preferably at least 1:1, and usually at most 10:1, preferably at most 5:1, more preferably at most 3:1.

In the copolymer, the butenediyl unit expressed by A and A' and the dioxy unit expressed by B, B' and/or B" are alternatively bonded.

A and A' are randomly selected in the butenediyl unit, and at least one A' is contained. A number of the butenediyl unit in the copolymer is at least 2. Also, the dioxy unit may have a structure having only one kind of B, B' and B", or may be a random mixture of at least two kinds of B, B' and B". Further, with regard to the terminal structure of the condensation copolymer, it is an acetoxy group or a hydroxyl group when the terminal unit of the condensation copolymer is the butenediyl unit expressed by A or A', and it is a hydrogen atom, an alkali metal ion, a phosphonium compound or an ammonium compound when the terminal unit of the condensation copolymer is the dioxy unit expressed by B, B' or B".

The condensation copolymer has a molecular weight of usually at least 200, preferably at least 300, more preferably at least 500, and usually at most 1,000,000, preferably at most 100,000, more preferably at least 10,000, most preferably at most 5,000.

According to the synthesis method of the present invention, the condensation copolymer is obtained by reacting 3,4-disubstituted 1-butene of the formula (b) or 1,4-disubstituted 2-butene of the formula (c) with a difunctional oxygen nucleophilic agent in the presence of the catalyst of the present invention. Preferable examples of the 3,4-disubstituted 1-butene of the formula (b) include 3,4-diacetoxy-1-butene, 3-acetoxy-4-hydroxy-1-butene, 4-acetoxy-3-hydroxy-1-butene, 3,4-dihydroxy-1-butene, and the like. Preferable examples of the 1,4-disubstituted 2-butene of the formula (c) include 1,4-diacetoxy-2-butene, 1-acetoxy-4-hydroxy-2-butene, 1,4-dihydroxy-2-butene, and the like. These compounds may be used alone or may be used in a mixture of two or more kinds.

The difunctional oxygen nucleophilic agent may be classified mainly into three groups depending on a kind of a dioxy unit in the condensation copolymer. For example, the difunctional oxygen nucleophilic agent corresponding to the dioxy unit B is diols, the difunctional oxygen nucleophilic agent corresponding to the dioxy unit B' is hydroxycarboxylic acids, and the difunctional oxygen nucleophilic agent corresponding to the dioxy unit B" is dicarboxylic acids. Examples of the diols include alkane diols such as ethylene glycol, 1,3-propane diol, 1,4-butane diol, 1,6-hexane diol, 2,4-dihydroxypentane, 2,2-diethyl-1,3-propane diol, and the like, alkene diols such as 1,4-dihydroxy-2-butene, 1,9-dihydroxy-3,6-nonadiene, and the like, alkyne diols such as 1,4-dihydroxy-2-butyne, 1,5-dihydroxy-3-heptyne, and the like, cycloalkane diols such as cyclohexane-1,4-diol, cyclopentane-1,3-diol, and the like, diphenol derivatives such as hydroquinone, 1,4-dihydroxynaphthalene, 2,6-dihydroxynaphthalene, 4,4,-dihydroxybiphenyl, 2,2-bis(4-hydroxyphenyl)propane, and the like, and further, 4-(2-hydroxyethyl)phenol, 1,4-dihydroxymethylbenzene, and the like. Also, examples of the hydroxycarboxylic acids include 3-hydroxy propionic acid, 4-hydroxy benzoic acid, 3-hydroxymethyl benzoic acid, 4-hydroxyphenyl acetic acid, and the like. Also, examples of the dicarboxylic acids include aliphatic dicarboxylic acids such as oxalic acid, malonic acid, succinic acid, glutaric acid, adipic acid or the like, and aromatic dicarboxylic acids such as phthalic acid, isophthalic acid, terephthalic acid, naphthalene-1,4-dicarboxylic acid, naphthalene-1,8-dicarboxylic acid, naphthalene-2,3-dicarboxylic acid, naphthalene-2,6-dicarboxylic acid or the like. With regard to the above difunctional oxygen nucleophilic agent, a specific compound may be used alone, or a mixture of two or more kinds may be used.

The production method of the condensation copolymer can be carried out by using the reaction between an allyl starting material compound and an oxygen nucleophilic agent in accordance with the present invention. However, when water or acetic acid by-produced depending on a reaction retains in the reaction system, the molecular weight of the condensation copolymer thus produced does not become large, and it is therefore preferable to proceed the reaction by removing acetic acid or water from the reaction system when it is desired to obtain the condensation copolymer having a larger molecular weight. Acetic acid or water can be removed from the reaction system by distillation under normal pressure or reduced pressure or by adding such a compound like calcium oxide as to form an insoluble salt by reacting with acetic acid or water.

Also, a method for removing a catalyst from the condensation copolymer thus obtained can be effectively carried out by distillation when the condensation copolymer product has a low molecular weight and can be distilled, but the catalyst is usually removed by a fractional precipitation method which comprises adding a poor solvent to the condensation copolymer to precipitate the condensation copolymer and separating a supernatant phase containing the catalyst. In such a case, the catalyst contained in the supernatant phase, the condensation copolymer having a low molecular weight and the starting material can be recycled into a reactor for reuse after removing the poor solvent from the supernatant phase by distillation, which is economically preferable. Also, when employing the fractional precipitation method, the condensation copolymer thus produced contains a poor solvent, and it is therefore necessary to remove the poor solvent by distillation.

The condensation copolymer of the present invention is characterized by having a structure having a double bond in the main chain and a side chain, and can work as a cross-linking agent by being added to other condensation copolymer or polymer to have the double bond reacted or can be used for producing a new polymer having a high function or performance by introducing a new functional group into the double bond of the condensation copolymer.

EXAMPLES

Hereinafter, the present invention is further fully illustrated by the following Examples, but should not be limited thereto.

Examples 1 to 2 and Comparative Examples 1 to 2

Allylphenyl ether synthesis reaction of the present invention was carried out by using allylmethyl carbonate as an allyl starting material compound and phenol as an oxygen nucleophilic agent.

A catalyst solution having a palladium concentration of 15.05 mmol/l was prepared by adding 0.0149 g (0.0151 mmol) of trisdibenzylideneacetone dipalladium having a palladium content of 21.5 wt % as a transition metal compound and the above (L-26) bidentate phosphite (Example 1) or the above (L-8) bidentate phosphite (Example 2) respectively in an amount of 4 equivalents (0.1204 mmol) to palladium as a multidentate coordinated phosphite compound to a container substituted with argon, adding 2.0 ml of tetrahydrofuran thereto and stirring the resultant mixture at room temperature. Thereafter, in order to carry out the reaction, another container was substituted with argon, and 5.0 ml of a tetrahydrofuran solution containing 0.1720 g (1.481 mmol) of allylmethyl carbonate and 0.2707 g (2.877 mmol) of phenol was added into the container under argon atmosphere. 20.0 µl of the above prepared catalyst solution was added thereto by a microsyringe, and the resultant mixture was heated at 60° C. to carry out the reaction. After reacting for 30 minutes, the resultant solution composition was analyzed by gas chromatography to determine a yield of allylphenyl ether.

As Comparative Examples, the same procedure was repeated by using conventionally used 1,4-bis(diphenylphosphino)butane (dppb) as a bidentate phosphine ligand (Comparative Example 1) and triphenylphosphite ligand as a monodentate coordinated phosphite ligand (Comparative Example 2). However, in the case of using the triphenyl phosphite which is a monodentate ligand, it was added in an amount of 8 equivalents to palladium.

The results are shown in the following Table 1.

TABLE 1

|  | Ligand | Allylphenyl ether yield |
| --- | --- | --- |
| Ex. 1 | (L-26) | 89% |
| Ex. 2 | (L-8) | 10% |
| Comp. Ex. 1 | Dppb | 4% |
| Comp. Ex. 2 | P(OPh)$_3$ | 3% |

Examples 3 to 5 and Comparative Examples 3 to 5

Allyloctyl ether synthesis reaction of the present invention was carried out by using allyl acetate as an allyl starting material compound and 1-octanol as an oxygen nucleophilic agent.

The reaction was carried out by adding 0.0048 g (0.0048 mmol) of trisdibenzylideneacetone dipalladium having a palladium content of 21.5 wt % as a transition metal compound and the above (L-26) bidentate phosphite compound (Example 3), the above (L-57) bidentate phosphite compound (Example 4) or the above (L-11) bidentate phosphite compound (Example 5) respectively in an amount of 2 equivalents (0.0194 mmol) to palladium as a multidentate coordinated phosphite compound to a container substituted with argon, adding 0.943 g (9.420 mmol) of allyl acetate and 2.422 g (18.594 mmol) of 1-octanol under argon atmosphere thereto, and heating the resultant mixture at 100° C. to carry out the reaction. After reacting for 60 minutes, the resultant solution composition was analyzed by gas chromatography to determine a yield of allyloctyl ether.

Also, as Comparative Examples, the same reaction procedure was repeated by using conventionally used 1,4-bis(diphenylphosphino)butane (dppb) as a bidentate phosphine ligand (Comparative Example 3), triphenyl phosphine as a monodentate phosphine ligand (Comparative Example 4), and triphenyl phosphite ligand as a monodentate coordinated phosphite ligand (Comparative Example 5). However, in the case of using a monodentate ligand, it was added in an amount of 4 equivalents to palladium.

The results are shown in the following Table 2.

TABLE 2

|  | Ligand | Allyloctyl ether yield |
| --- | --- | --- |
| Ex. 3 | (L-26) | 91% |
| Ex. 4 | (L-57) | 92% |
| Ex. 5 | (L-11) | 82% |
| Comp. Ex. 3 | Dppb | 7% |
| Comp. Ex. 4 | PPh$_3$ | 7% |
| Comp. Ex. 5 | P(OPh)$_3$ | 3% |

Examples 6 to 7 and Comparative Examples 6 to 7

Allyl benzoate synthesis reaction of the present invention was carried out by using allyl acetate as an allyl starting material compound and benzoic acid as an oxygen nucleophilic agent.

A catalyst solution having a palladium concentration of 15.05 mmol/l was prepared by adding 0.0149 g (0.0151 mmol) of trisdibenzylideneacetone dipalladium having a palladium content of 21.5 wt % as a transition metal compound and the above (L-54) bidentate phosphite compound (Example 6) or the above (L-12) bidentate phosphite compound (Example 7) respectively in an amount of 4 equivalents (0.1204 mmol) to palladium as a multidentate coordinated phosphite compound to a container substituted with argon, adding 2.0 ml of tetrahydrofuran thereto, and stirring the resultant mixture at room temperature. Thereafter, in order to carry out the reaction, another container was substituted with argon, and 4.0 ml of a tetrahydrofuran solution containing 0.3083 g (2.525 mmol) of benzoic acid and 0.1208 g (1.206 mmol) of allyl acetate was added thereto under argon atmosphere. 60.0 µl of the above prepared catalyst solution was added thereto by a microsyringe, and the resultant mixture was heated at 60° C. to carry out the reaction. After reacting for 30 minutes, the resultant solution composition was analyzed by gas chromatography to determine a yield of allyl benzoate.

Also, as Comparative Examples, the same reaction procedure was repeated by using conventionally used 1,4-bis(diphenylphosphino)butane (dppb) as a bidentate phosphine ligand (Comparative Example 6) and triphenyl phosphite ligand as a monodentate coordinated phosphite ligand (Comparative Example 8). However, in the case of using the monodentate ligand, it was added in an amount of 8 equivalents to palladium.

The results are shown in the following Table 3.

TABLE 3

|  | Ligand | Allyl benzoate yield |
| --- | --- | --- |
| Ex. 6 | (L-54) | 42% |
| Ex. 7 | (L-12) | 38% |
| Comp. Ex. 6 | Dppb | 1% |
| Comp. Ex. 7 | P(OPh)$_3$ | 21% |

Example 8

Butylbutenyl ethers synthesis reaction of the present invention was carried out by using cis-1,4-diacetoxy-2-butene as an allyl starting material compound and 1-butanol as an oxygen nucleophilic agent.

The reaction was carried out by adding 0.0020 g (0.0040 mmol) of trisdibenzylideneacetone dipalladium having a palladium content of 21.5 wt % and 0.0173 g (0.0162 mmol) of the above (L-26) bidentate phosphite in an amount of 4 equivalents to a container substituted with nitrogen, adding 1.418 g (8.233 mmol) of cis-1,4-diacetoxy-2-butene and 2.327 g (31.395 mmol) of 1-butanol thereto under nitrogen atmosphere, and heating the resultant mixture at 100° C. After reacting 5 hours, the resultant solution composition was analyzed by gas chromatography, and it was found that cis-1,4-diacetoxy-2-butene was converted at a conversion rate of 97.5%, and 71.8% of dibutoxybutene and 25.7% of acetoxybutoxybutene were produced.

Particularly, among the 71.8% dibutoxybutene thus produced, 56.0% of 1,4-dibutoxy-2-butene (mixture of cis and trans) and 15.8% of 3,4-dibutoxy-1-butene were formed, and among the 25.7% acetoxybutoxybutene thus produced, 12.6% of 1-acetoxy-4-butoxy-2-butene (mixture of cis and trans), 4.9% of 3-acetoxy-4-butoxy-1-butene and 8.2% of 4-acetoxy-3-butoxy-1-butene were formed.

Example 9

Phenylbutenyl ethers synthesis reaction of the present invention was carried out by using cis-1,4-diacetoxy-2-butene as an allyl starting material compound and phenol as an oxygen nucleophilic agent.

The reaction was carried out by adding 0.0020 g (0.0044 mmol) of trisdibenzylideneacetone dipalladium having a palladium content of 21.5 wt % and 0.0187 g (0.0175 mmol) of the above (L-26) bidentate phosphite in an amount of 4 equivalents to a container substituted with nitrogen, adding 1.460 g (8.477 mmol) of cis-1,4-diacetoxy-2-butene and 3.164 g (33.615 mmol) of phenol thereto under nitrogen atmosphere, and heating the resultant mixture at 100° C.

After reacting 60 minutes, the resultant solution composition was analyzed by gas chromatography, and it was found that cis-1,4-diacetoxy-2-butene was converted at a conversion rate of 75.2%, and 14.9% of dephenoxy and 59.8% of acetoxyphenoxybutene were produced.

Particularly, among the 14.9% diphenoxybutene thus produced, 13.9% of 1,4-diphenoxy-2-butene (mixture of cis and trans) and 1.0% of 3,4-diphenoxy-1-butene were formed, and among the 59.8% acetoxyphenoxybutene thus produced, 37.8% of 1-acetoxy-4-phenoxy-2-butene (mixture of cis and trans), 11.1% of 3-acetoxy-4-phenoxy-1-butene and 10.9% of 4-acetoxy-3-phenoxy-1-butene were formed.

Example 10

The present invention was applied to synthesis reaction of an unsaturated bond-containing polyester oligomer by using cis-1,4-diacetoxy-2-butene as an allyl starting material compound and adipic acid (difunctional carboxylic acid) as an oxygen nucleophilic agent.

The reaction was carried out by adding 0.0074 g (0.0162 mmol) of trisdibenzylideneacetone dipalladium is having a palladium content of 21.5 wt % and 0.0693 g (0.0647 mmol) of the above (L-26) bidentate phosphite in an amount of 4 equivalents to a two-forked round bottom flask substituted with nitrogen, adding 10.005 g (58.107 mmol) of cis-1,4-diacetoxy-2-butene and 7.104 g (48.610 mmol) of adipic acid thereto under nitrogen atmosphere, and heating the resultant mixture at 100° C. under a reduced pressure of 50 mmHg. As the reaction proceeds, the pressure in the system was gradually lowered to 20 mmHg (after 1 hour) and to 7 mmHg (after three hours), and acetic acid formed was removed from the system under the reduced pressure by distillation. After reacting for 7 hours; the resultant solution composition was analyzed by gas chromatography, and it was found that cis-1,4-diacetoxy-2-butene was converted at a conversion rate of almost 100% to obtain a syrup-like oligomer. The oligomer thus obtained was analyzed by gel permeation chromatography to determine a molecular weight distribution, and it was found that the oligomer was a polyester oligomer having a molecular weight of 4,000 at the main central portion and a maximum molecular weight of 10,000 in terms of polystyrene molecular weight.

Example 11

The present invention was applied to synthesis reaction of an unsaturated bond-containing polyether oligomer by using cis-1,4-diacetoxy-2-butene as an allyl starting material compound and 1,4-butane diol (difunctional alcohol) as an oxygen nucleophilic agent.

The reaction was carried out by adding 0.0572 g (0.1249 mmol) of trisdibenzylideneacetone dipalladium having a palladium content of 21.5 wt % and 0.2670 g (0.2492 mmol) of the above (L-26) bidentate phosphite in an amount of 2 equivalents to a two-forked round bottom flask substituted with nitrogen, adding 17.221 g (100.016 mmol) of cis-1,4-diacetoxy-2-butene and 9.012 g (100.000 mmol) of 1,4-butane diol thereto under nitrogen atmosphere, and heating the resultant mixture at 100° C. while gradually reducing a pressure from 50 mmHg in the same manner as in Example 10. After reacting for 7 hours, the resultant solution composition was analyzed by gas chromatography, and it was found that cis-1,4-diacetoxy-2-butene was converted at a conversion rate of almost 100% to obtain a syrup-like oligomer. The oligomer thus obtained was analyzed by gel permeation chromatography to determine a molecular weight distribution, and it was found that the oligomer was a polyether oligomer having a molecular weight of 2,400 at the main central portion and a maximum molecular weight of 7,000 in terms of polystyrene molecular weight.

Example 12

The present invention was applied to synthesis reaction of an unsaturated bond-containing polyether oligomer by using cis-1,4-diacetoxy-2-butene as an allyl starting material compound and 2,2-bis(4-hydroxyphenyl)propane (difunctional phenol: bisphenol A) as an oxygen nucleophilic agent.

The reaction was carried out by adding 0.0091 g (0.0199 mmol) of trisdibenzylideneacetone dipalladium having a palladium content of 21.5 wt % and 0.0852 g (0.0795 mmol) of the above (L-26) bidentate phosphite in an amount of 4 equivalents to a two-forked round bottom flask substituted with nitrogen, adding 10.008 g (58.126 mmol) of cis-1,4-diacetoxy-2-butene and 11.001 g (48.189 mmol) of bisphenol A thereto under nitrogen atmosphere, and heating the resultant mixture at 100° C. while gradually reducing a pressure from 50 mmHg in the same manner as in Example 10. After reacting for 7 hours, the resultant solution composition was analyzed by gas chromatography, and it was found that cis-1,4-diacetoxy-2-butene was converted at a conversion rate of almost 100% to obtain a thick syrup-like oligomer. The oligomer thus obtained was analyzed by gel permeation chromatography to determine a molecular weight distribution, and it was found that the oligomer was a polyether oligomer having a molecular weight of 3,200 at the main central portion and a maximum molecular weight of 7,000 in terms of polystyrene molecular weight.

As evident from the above results, a catalyst comprising the bidentate phosphite type ligand of the present invention provides a higher catalytic activity as compared with that of a catalyst comprising conventionally used bidentate phosphine type ligand or a triaryl type monodentate phosphite ligand.

(Examples using a Phosphonium Compound in the Reaction System are Illustrated Below.)

Example 13 and Example 14

The present invention was applied to a reaction for producing allylphenyl ether by carrying out allylation reaction by using allylmethyl carbonate as an allyl starting material compound and phenoxide as a nucleophilic agent in the presence of a catalyst of palladium-bidentate phosphite (L-26).

A catalyst solution having a palladium concentration of 15.05 mmol/l was prepared by adding 0.0149 g (0.0151 mmol) of trisdibenzylideneacetone dipalladium having a palladium content of 21.5 wt % as a transition metal compound and 0.1291 g (0.1205 mmol) of the above (L-26) compound as a bidentate phosphite compound to a container substituted with argon, adding 2.0 ml of tetrahydrofuran thereto, and stirring the resultant mixture at room temperature. Thereafter, in order to carry out the reaction, another container was substituted with argon, and 4.45 g of a tetrahydrofuran solution containing 3.85 wt % of allylmethyl carbonate and 6.06 wt % of phenol was added into the container. 5 μl of the above prepared catalyst solution was added thereto by a microsyringe, and the resultant mixture was heated at 60° C. to carry out the reaction (Example 13: reaction in the absence of a phosphonium compound). Evaluation of the reaction rate was carried out by analyzing the solution composition by gas chromatography before and after the reaction to determine a conversion rate of allylmethyl carbonate, and applying the value thus determined to the following calculation formula to calculate a reaction rate constant. In this case, the reaction is considered to be a pseudo-primary reaction by ignoring an influence by a concentration change of phenol to calculate a reaction rate: k in accordance with the following calculation formula. In the following calculation formula, conv. represents a conversion rate of allylmethyl carbonate and t represents its reaction time (unit: hour).

$k = -1n(1-\text{conv.})/t$

Also, a reaction was carried out in a system of further containing tetra(n-butyl)phosphonium acetate salt respectively in an amount of 200 equivalents to Pd, under the same conditions as in the above Example 13 (Example 14: the reaction system in the presence of a phosphonium compound). The results are shown in the following Table 4.

TABLE 4

| | Phosphonium compound | Reaction rate constant (h$^{-1}$) | Specific activity |
|---|---|---|---|
| Ex. 13 | — | 0.59 | 1.00 |
| Ex. 14 | [P(n-Bu)$_4$]$^+$[OAc]$^-$ | 1.81 | 3.07 |

As evident from the above results, it is proved that the presence of a phosphonium compound in the reaction system can improve the reaction activity.

(The Following Examples Illustrate the Presence of an Ammonium Compound in the Reaction System.)

Example 15 and Example 16

The present invention was applied to a reaction for producing allylphenyl ether by carrying out allylation reaction by using allylmethyl carbonate as an allyl starting material compound and phenoxide as a nucleophilic agent in the presence of a catalyst of palladium-bidentate phosphite (L-26).

A catalyst solution having a palladium concentration of 15.05 mmol/l was prepared by adding 0.0149 g (0.0151 mmol) of trisdibenzylideneacetone dipalladium having a palladium content of 21.5 wt % as a transition metal compound and 0.1291 g (0.1205 mmol) of the above (L-26) compound as a bidentate phosphite compound to a container substituted with argon, adding 2.0 ml of tetrahydrofuran thereto, and stirring the resultant mixture at room temperature. Thereafter, in order to carry out the reaction, another container was substituted with argon, and 4.45 g of a tetrahydrofuran solution containing 3.85 wt % of allylmethyl carbonate and 6.06 wt % of phenol was added into the container. 5 μl of the above prepared catalyst solution was added thereto by a microsyringe, and the resultant mixture was heated at 60° C. to carry out the reaction (Example 15: reaction in the absence of a counter cation). Evaluation of the reaction rate was carried out in the same manner as in Examples 13 and 14.

Also, a reaction was carried out in a system of further adding DBU to prepare an ammonium compound respectively in an amount of 200 equivalents to Pd, under the same conditions as in the above Example 15 (Example 16: the reaction system in the presence of an ammonium compound). The results are shown in the following Table 5.

TABLE 5

| | Ammonium compound | Reaction rate constant (h$^{-1}$) | Specific activity |
|---|---|---|---|
| Ex. 15 | — | 0.59 | 1.00 |
| Ex. 16 | [DBU-H]$^+$[OAc]$^-$ | 1.51 | 2.56 |

As evident from the above results, it is proved that the presence of an ammonium compound in the reaction system can improve the reaction activity.

According to the method for producing an allyl compound by the present invention, various allyl compounds can be efficiently produced as compared with a method of using a conventional catalyst system since a new catalyst system achieving a sufficiently higher catalytic activity to an oxygen nucleophilic agent having a low reactivity is used in the production of a new allyl compound by reacting an allyl starting material compound and a nucleophilic agent.

The entire disclosures of Japanese Patent Application No. 2002-252900 filed on Aug. 30, 2002, Japanese Patent Application No. 2002-260452 filed on Sep. 5, 2002 and Japanese Patent Application No. 2002-261870 filed on Sep. 6, 2002 including specifications, claims and summaries are incorporated herein by reference in their entireties.

What is claimed is:

1. A condensation copolymer containing:
   a butenediyl unit expressed by the following formulae A and A', and
   a dioxy unit expressed by the following formulae B, B' and/or B",

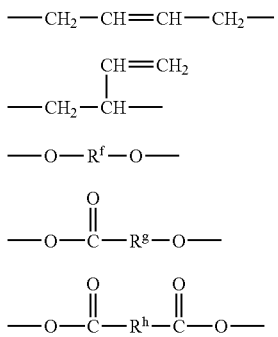

wherein $R^f$, $R^g$ and $R^h$ are respectively independently a bivalent organic group which may have a substituent, wherein the number of butenediyl units is at least two.

2. The condensation copolymer according to claim 1, wherein the butenediyl unit expressed by the formula A and the butenediyl unit expressed by the formula A' are present in a mol ratio of A:A'=1:10–10:1 in the copolymer.

3. The condensation copolymer of claim 1, wherein the dioxy unit is only B.

4. The condensation copolymer of claim 1, wherein the dioxy unit is only B'.

5. The condensation copolymer of claim 1, wherein the dioxy unit is only B".

6. The condensation copolymer of claim 1, wherein the dioxy unit is a mixture of B and B'.

7. The condensation copolymer of claim 1, wherein the dioxy unit is a mixture of B and B".

8. The condensation copolymer of claim 1, wherein the dioxy unit is a mixture of B' and B".

9. The condensation copolymer of claim 1, wherein the dioxy unit is a mixture of B, B' and B".

10. The condensation copolymer of claim 1, which has a molecular weight of at least 200.

11. The condensation copolymer of claim 1, which has a molecular weight of at least 500.

12. The condensation copolymer of claim 1, which has a molecular weight ranging from 500–5,000.

13. The condensation copolymer of claim 1, which has a molecular weight of at most 100,000.

14. A method for crosslinking a polymer or copolymer comprising:
contacting said polymer or copolymer with the condensation copolymer of claim 1 and
crosslinking said polymer or copolymer by reaction with the double bond of the condensation copolymer of claim 1.

15. A method for introducing a functional group into a polymer or copolymer comprising:
contacting the condensation copolymer of claim 1 with a molecule containing a functional group and
introducing the functional group into a double bond of the condensation copolymer.

16. The condensation copolymer of claim 1, wherein A and A' are randomly selected in the butenediyl unit, but at least one A' is contained.

17. The condensation copolymer of claim 1, wherein a terminal structure of the condensation polymer is an acetoxy group when A or A' is the terminal unit.

18. The condensation copolymer of claim 1, wherein a terminal structure of the condensation polymer is a hydroxy group when A or A' is the terminal unit.

19. The condensation copolymer of claim 1, wherein a terminal structure of the condensation polymer is hydrogen when dioxy unit B, B' or B' is the terminal unit.

20. The condensation copolymer of claim 1, wherein a terminal structure of the condensation polymer is an alkali metal ion when dioxy unit B, B' or B' is the terminal unit.

21. The condensation copolymer of claim 1, wherein a terminal structure of the condensation polymer is a phosphonium compound when dioxy unit B, B' or B' is the terminal unit.

22. The condensation copolymer of claim 1, wherein a terminal structure of the condensation polymer is an ammonium compound when dioxy unit B, B' or B' is the terminal unit.

23. The condensation copolymer of claim 1, wherein the ratio of A:A' is at least 1:10.

24. The condensation copolymer of claim 1, wherein the ratio of A:A' is at most 10:1.

* * * * *